US012770734B2

(12) United States Patent
McFarland, Jr.

(10) Patent No.: US 12,770,734 B2
(45) Date of Patent: *Oct. 20, 2026

(54) LINKING PERSONAL ENVIRONMENT AND TRANSPORT OPERATION

(71) Applicant: TOYOTA MOTOR NORTH AMERICA, INC., Plano, TX (US)

(72) Inventor: Stephen Paul McFarland, Jr., Allen, TX (US)

(73) Assignee: TOYOTA MOTOR NORTH AMERICA, INC., Plano, TX (US)

(*) Notice: Subject to any disclaimer, the term of this patent is extended or adjusted under 35 U.S.C. 154(b) by 105 days.

This patent is subject to a terminal disclaimer.

(21) Appl. No.: 18/888,118

(22) Filed: Sep. 17, 2024

(65) Prior Publication Data

US 2025/0014746 A1 Jan. 9, 2025

Related U.S. Application Data

(63) Continuation of application No. 17/405,622, filed on Aug. 18, 2021, now Pat. No. 12,112,851.

(51) Int. Cl.

| | |
|---|---|
| ***G16H 40/67*** | (2018.01) |
| ***A61B 5/18*** | (2006.01) |
| ***B60W 60/00*** | (2020.01) |
| ***G08B 21/06*** | (2006.01) |

(52) U.S. Cl.

CPC ............... *G16H 40/67* (2018.01); *A61B 5/18* (2013.01); *B60W 60/0016* (2020.02); *B60W 60/0017* (2020.02); *G08B 21/06* (2013.01)

(58) Field of Classification Search

CPC .............. G16H 40/67; B60W 60/0016; B60W 60/0017; A61B 5/18; G08B 21/06

See application file for complete search history.

(56) References Cited

U.S. PATENT DOCUMENTS

| | | | | |
|---|---|---|---|---|
| 7,930,564 | B2 * | 4/2011 | Arai | G06F 1/3203 713/300 |
| 8,560,128 | B2 * | 10/2013 | Ruff | G06F 3/04842 700/278 |
| 8,576,081 | B2 | 11/2013 | Hatakeyama et al. | |
| 8,768,573 | B2 | 7/2014 | Breed | |
| 8,836,491 | B2 * | 9/2014 | Rao | B60H 1/00778 340/426.26 |
| 9,124,955 | B2 | 9/2015 | Geva et al. | |
| 9,418,554 | B2 | 8/2016 | Velusamy et al. | |
| 9,509,957 | B2 | 11/2016 | Higgins-Luthman et al. | |
| 9,650,041 | B2 | 5/2017 | Feit et al. | |

(Continued)

FOREIGN PATENT DOCUMENTS

| | | |
|---|---|---|
| CN | 105073474 B | 12/2017 |

OTHER PUBLICATIONS

Notice of Allowance issued in the Parent U.S. Appl. No. 17/405,622, mailed on Jun. 4, 2024.

(Continued)

*Primary Examiner* — Gertrude Arthur Jeanglaude

(57) ABSTRACT

An example operation includes one or more of determining a reaction by at least one occupant of a transport, related to a most relevant data of the transport, and sending a notification of the reaction and the data to a display associated with the at least one occupant, when the reaction is greater than a threshold.

20 Claims, 26 Drawing Sheets

(56) References Cited

U.S. PATENT DOCUMENTS

| | | | |
|---|---|---|---|
| 9,955,326 | B2 | 4/2018 | Avrahami et al. |
| 9,956,963 | B2 | 5/2018 | Kumar et al. |
| 10,118,628 | B2 | 11/2018 | Lundsgaard |
| 10,127,810 | B2 | 11/2018 | Durie, Jr. et al. |
| 10,252,713 | B2 | 4/2019 | Yoshida et al. |
| 10,308,258 | B2 | 6/2019 | Fung et al. |
| 10,390,748 | B2 | 8/2019 | Lee et al. |
| 10,430,695 | B2 | 10/2019 | Sathyanarayana et al. |
| 11,345,415 | B2 * | 5/2022 | Funyak .................. G08B 21/22 |
| 12,418,585 | B2 * | 9/2025 | Moss ...................... H04W 4/33 |
| 2014/0276090 | A1 | 9/2014 | Breed |
| 2015/0057557 | A1 | 2/2015 | Howie et al. |
| 2016/0318521 | A1 | 11/2016 | Nothacker et al. |
| 2017/0072850 | A1 | 3/2017 | Curtis et al. |
| 2017/0146801 | A1 | 5/2017 | Stempora |

OTHER PUBLICATIONS

Non Final Office Action issued in the Parent U.S. Appl. No. 17/405,622, mailed on Feb. 7, 2024.

* cited by examiner

100

200

210

265

290A

290B

290D

290E

290E

320

340

550

600

LINKING PERSONAL ENVIRONMENT AND TRANSPORT OPERATION

CROSS-REFERENCE TO RELATED APPLICATIONS

This application is a continuation of U.S. patent application Ser. No. 17/405,622, filed on Aug. 18, 2021, the entire disclosure of which is incorporated by reference herein.

BACKGROUND

Vehicles or transports, such as cars, motorcycles, trucks, planes, trains, etc., generally provide transportation needs to occupants and/or goods in a variety of ways. Functions related to transports may be identified and utilized by various computing devices, such as a smartphone or a computer located on and/or off the transport.

SUMMARY

One example embodiment provides a method that includes one or more of determining a reaction by at least one occupant of a transport, related to a most relevant data of the transport, and sending a notification of the reaction and the data to a display associated with the at least one occupant, when the reaction is greater than a threshold.

Another example embodiment provides a system that includes a memory communicably coupled to a processor, wherein the processor performs one or more of determine a reaction by at least one occupant of a transport, related to a most relevant data of the transport, and send a notification of the reaction and the data to a display associated with the at least one occupant, when the reaction is greater than a threshold.

A further example embodiment provides a non-transitory computer readable medium comprising instructions, that when read by a processor, cause the processor to perform one or more of the transport, and sending a notification of the reaction and the data to a display associated with the at least one occupant, when the reaction is greater than a threshold.

DETAILED DESCRIPTION

Figure 1:
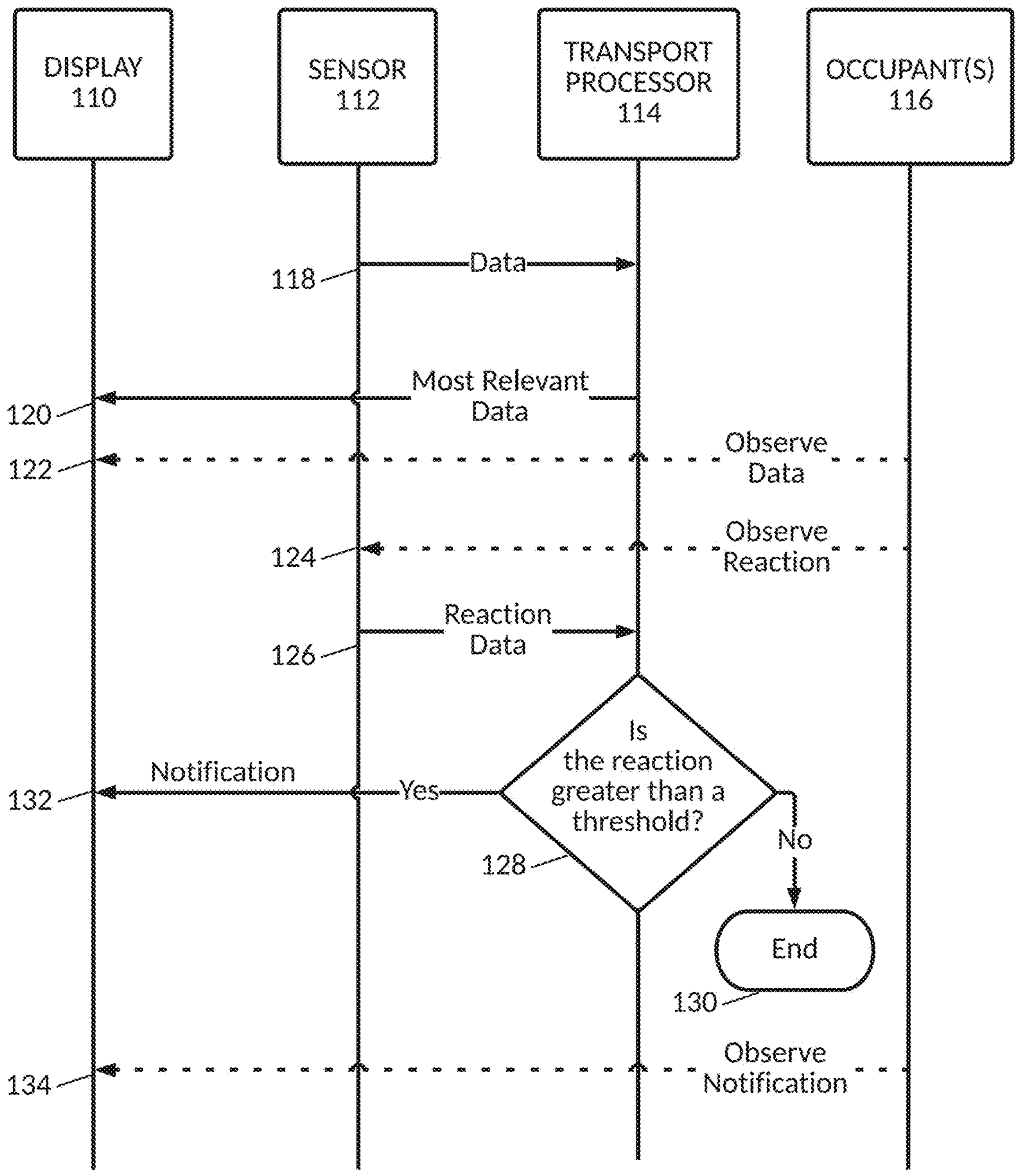
FIG. 1 illustrates an example flowchart, according to example embodiments.

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed but is merely representative of selected embodiments.

Communications between the transport(s) and certain entities, such as remote servers, other transports and local computing devices (e.g., smartphones, personal computers, transport-embedded computers, etc.) may be sent and/or received, and processed by one or more 'components' which may be hardware, firmware, software or a combination thereof. The components may be part of any of these entities or computing devices or certain other computing devices. In one example, consensus decisions related to blockchain transactions may be performed by one or more computing devices or components (which may be any element described and/or depicted herein) associated with the transport(s) and one or more of the components outside or at a remote location from the transport(s).

The instant features, structures, or characteristics as described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments. In the diagrams, any connection between elements can permit one-way and/or two-way communication even if the depicted connection is a one-way or two-way arrow. In the current solution, a transport may include one or more of cars, trucks, walking area battery electric vehicle (BEV), e-Palette, fuel cell bus, motorcycles, scooters, bicycles, boats, recreational vehicles, planes, and any object that may be used to transport people and or goods from one location to another.

In addition, while the term "message" may have been used in the description of embodiments, other types of network data, such as, a packet, frame, datagram, etc. may also be used. Furthermore, while certain types of messages and signaling may be depicted in exemplary embodiments they are not limited to a certain type of message and signaling.

Example embodiments provide methods, systems, components, non-transitory computer readable medium, devices, and/or networks, which provide at least one of: a transport (also referred to as a vehicle or car herein), a data collection system, a data monitoring system, a verification system, an authorization system and a vehicle data distribution system. The vehicle status condition data, received in the form of communication messages, such as wireless data network communications and/or wired communication messages, may be processed to identify vehicle/transport status conditions and provide feedback as to the condition and/or changes of a transport. In one example, a user profile may be applied to a particular transport/vehicle to authorize a current vehicle event, service stops at service stations, to authorize subsequent vehicle rental services, and enable vehicle to vehicle communications.

Within the communication infrastructure, a decentralized database is a distributed storage system, which includes multiple nodes that communicate with each other. A blockchain is an example of a decentralized database, which includes an append-only immutable data structure (i.e. a distributed ledger) capable of maintaining records between untrusted parties. The untrusted parties are referred to herein as peers, nodes or peer nodes. Each peer maintains a copy of the database records and no single peer can modify the database records without a consensus being reached among the distributed peers. For example, the peers may execute a consensus protocol to validate blockchain storage entries, group the storage entries into blocks, and build a hash chain via the blocks. This process forms the ledger by ordering the storage entries, as is necessary, for consistency. In a public or permissionless blockchain, anyone can participate without a specific identity. Public blockchains can involve crypto-currencies and use consensus based on various protocols such as proof of work (PoW). Conversely, a permissioned blockchain database can secure interactions among a group of entities, which share a common goal, but which do not or cannot fully trust one another, such as businesses that exchange funds, goods, information, and the like. The instant solution can function in a permissioned and/or a permissionless blockchain setting.

Smart contracts are trusted distributed applications, which leverage tamper-proof properties of the shared or distributed ledger (which may be in the form of a blockchain) and an underlying agreement between member nodes, which is referred to as an endorsement or endorsement policy. In general, blockchain entries are "endorsed" before being committed to the blockchain while entries, which are not endorsed are disregarded. A typical endorsement policy allows smart contract executable code to specify endorsers for an entry in the form of a set of peer nodes that are necessary for endorsement. When a client sends the entry to the peers specified in the endorsement policy, the entry is executed to validate the entry. After validation, the entries enter an ordering phase in which a consensus protocol is used to produce an ordered sequence of endorsed entries grouped into blocks.

Nodes are the communication entities of the blockchain system. A "node" may perform a logical function in the sense that multiple nodes of different types can run on the same physical server. Nodes are grouped in trust domains and are associated with logical entities that control them in various ways. Nodes may include different types, such as a client or submitting-client node, which submits an entry-invocation to an endorser (e.g., peer), and broadcasts entry-proposals to an ordering service (e.g., ordering node). Another type of node is a peer node, which can receive client submitted entries, commit the entries and maintain a state and a copy of the ledger of blockchain entries. Peers can also have the role of an endorser. An ordering-service-node or orderer is a node running the communication service for all nodes, and which implements a delivery guarantee, such as a broadcast to each of the peer nodes in the system when committing entries and modifying a world state of the blockchain. The world state can constitute the initial blockchain entry, which normally includes control and setup information.

A ledger is a sequenced, tamper-resistant record of all state transitions of a blockchain. State transitions may result from smart contract executable code invocations (i.e., entries) submitted by participating parties (e.g., client nodes, ordering nodes, endorser nodes, peer nodes, etc.). An entry may result in a set of asset key-value pairs being committed to the ledger as one or more operands, such as creates, updates, deletes, and the like. The ledger includes a blockchain (also referred to as a chain), which is used to store an immutable, sequenced record in blocks. The ledger also includes a state database, which maintains a current state of the blockchain. There is typically one ledger per channel. Each peer node maintains a copy of the ledger for each channel of which they are a member.

A chain is an entry log structured as hash-linked blocks, and each block contains a sequence of N entries where N is equal to or greater than one. The block header includes a hash of the blocks' entries, as well as a hash of the prior block's header. In this way, all entries on the ledger may be sequenced and cryptographically linked together. Accordingly, it is not possible to tamper with the ledger data without breaking the hash links. A hash of a most recently added blockchain block represents every entry on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys that are included in the chain entry log. Since the current state represents the latest key values known to a channel, it is sometimes referred to as a world state. Smart contract executable code invocations execute entries against the current state data of the ledger. To make these smart contract executable code interactions efficient, the latest values of the keys may be stored in a state database. The state database may be simply an indexed view into the chain's entry log and can therefore be regenerated from the chain at any time. The state database may automatically be recovered (or generated if needed) upon peer node startup, and before entries are accepted.

A blockchain is different from a traditional database in that the blockchain is not a central storage but rather a decentralized, immutable, and secure storage, where nodes must share in changes to records in the storage. Some properties that are inherent in blockchain and which help implement the blockchain include, but are not limited to, an immutable ledger, smart contracts, security, privacy, decentralization, consensus, endorsement, accessibility, and the like.

Example embodiments provide a service to a particular vehicle and/or a user profile that is applied to the vehicle. For example, a user may be the owner of a vehicle or the operator of a vehicle owned by another party. The vehicle may require service at certain intervals and the service needs may require authorization prior to permitting the services to be received. Also, service centers may offer services to vehicles in a nearby area based on the vehicle's current route plan and a relative level of service requirements (e.g., immediate, severe, intermediate, minor, etc.). The vehicle needs may be monitored via one or more vehicle and/or road sensors or cameras, which report sensed data to a central controller computer device in and/or apart from the vehicle. This data is forwarded to a management server for review and action. A sensor may be located on one or more of the interior of the transport, the exterior of the transport, on a fixed object apart from the transport, and on another transport proximate the transport. The sensor may also be associated with the transport's speed, the transport's braking, the transport's acceleration, fuel levels, service needs, the gear-shifting of the transport, the transport's steering, and the like. A sensor, as described herein, may also be a device, such as a wireless device in and/or proximate to the transport. Also, sensor information may be used to identify whether the vehicle is operating safely and whether an occupant has engaged in any unexpected vehicle conditions, such as during a vehicle access and/or utilization period. Vehicle information collected before, during and/or after a vehicle's operation may be identified and stored in a transaction on a shared/distributed ledger, which may be generated and committed to the immutable ledger as determined by a permission granting consortium, and thus in a "decentralized" manner, such as via a blockchain membership group.

Each interested party (i.e., owner, user, company, agency, etc.) may want to limit the exposure of private information, and therefore the blockchain and its immutability can be used to manage permissions for each particular user vehicle profile. A smart contract may be used to provide compensation, quantify a user profile score/rating/review, apply vehicle event permissions, determine when service is needed, identify a collision and/or degradation event, identify a safety concern event, identify parties to the event and provide distribution to registered entities seeking access to such vehicle event data. Also, the results may be identified, and the necessary information can be shared among the registered companies and/or individuals based on a consensus approach associated with the blockchain. Such an approach could not be implemented on a traditional centralized database.

Various driving systems of the instant solution can utilize software, an array of sensors as well as machine learning functionality, light detection and ranging (LIDAR) projectors, radar, ultrasonic sensors, etc. to create a map of terrain and road that a transport can use for navigation and other purposes. In some embodiments, GPS, maps, cameras, sensors and the like can also be used in autonomous vehicles in place of LIDAR.

The instant solution includes, in certain embodiments, authorizing a vehicle for service via an automated and quick authentication scheme. For example, driving up to a charging station or fuel pump may be performed by a vehicle operator or an autonomous transport and the authorization to receive charge or fuel may be performed without any delays provided the authorization is received by the service and/or charging station. A vehicle may provide a communication signal that provides an identification of a vehicle that has a currently active profile linked to an account that is authorized to accept a service, which can be later rectified by compensation. Additional measures may be used to provide further authentication, such as another identifier may be sent from the user's device wirelessly to the service center to replace or supplement the first authorization effort between the transport and the service center with an additional authorization effort.

Data shared and received may be stored in a database, which maintains data in one single database (e.g., database server) and generally at one particular location. This location is often a central computer, for example, a desktop central processing unit (CPU), a server CPU, or a mainframe computer. Information stored on a centralized database is typically accessible from multiple different points. A centralized database is easy to manage, maintain, and control, especially for purposes of security because of its single location. Within a centralized database, data redundancy is minimized as a single storing place of all data also implies that a given set of data only has one primary record. A blockchain may be used for storing transport-related data and transactions.

Any of the actions described herein may be performed by one or more processors (such as a microprocessor, a sensor, an Electronic Control Unit (ECU), a head unit, and the like) which may be located on-board or off-board the transport. The one or more processors may communicate with other processors on-board or off-board other transports to utilize data being sent by the transport. The one or more processors and the other processors can send data, receive data, and utilize this data to perform one or more of the actions described or depicted herein.

Data presented to a driver or occupant of a transport may cause a reaction from the person digesting the data. This reaction, when examined in context, may be compared against a threshold value to determine if there may exist a condition where a level of safety of the transport could be raised by the additional functionality of the current application. The current application executing on at least one processor of a transport determines a reaction of an occupant to a most relevant data of the transport. When the value of a reaction of the occupant is greater than a threshold value, the current application sends a notification containing both the data and the reaction to the data to the occupant and/or other occupants in the transport.

FIG. 1 illustrates a flowchart 100, according to example embodiments. A transport processor 114 is presented that is a processor (such as a transport computer), which may be considered to be a main computer in a transport. The transport may be any moveable object that transfers persons and/or goods from one location to another and may be partially or wholly powered by electricity. Sensors 112, which may be cameras, radar devices, Electronic Control Units (ECUs), or like devices that control and/or detect various functions of the transport and communicate status and other data to the transport processor 114. The sensors may also send data in messages via a bus, such as a CAN bus, wherein the data may include images, video, and the like. A CAN bus system of the transport enables sensors, such as an ECU to communicate with all other sensors/ECUs. An ECU can prepare and broadcast information (e.g., sensor data) via the CAN bus (consisting of two wires, CAN low and CAN high). The transport processor 114 (otherwise referred to in the art as an engine control module (ECM)) or other processors on the transport, may communicate with other processors outside of the transport, such as servers, networks, and the like. In one embodiment, the transport processor 114 may itself be an ECU. A display 110 is any device on the transport that presents data that can be viewable by occupants in the transport. The display may be in various locations inside the transport included but not limited to a window of the transport (such as a heads-up display), behind the steering wheel on the dash, part of the infotainment system such as in the center of the front of the vehicle, on seatbacks such as displays that are viewable by occupants in the rear seats.

The current application may reside wholly or partially in one or more of the transport processor 114, a sensor such as an ECU, an infotainment system any other element in the transport containing a processor and memory. Data 118, such as data related to the occupants 116 and/or functionalities of the transport is sent from the sensors to the transport processor 114. This may be sent at determined times as predefined by the code in the sensor 112, in one embodiment. The transport processor 114 may determine a most relevant data from the data received from the at least one sensor 112. In one embodiment, this is determined by assigning and storing in the memory of the transport computer (executing in the transport processor 114) the received data from the sensors/ECUs 112 a value where the value is associated with how the data is related to one or more the following non-inclusive list: the performance of the transport, the safety of the transport, and the amount of time until the issue causes a severe situation with the transport. In one embodiment, the data that has the highest value is the most relevant. In other embodiments, data associated with the safety of the transport is the most relevant data, and/or data associated with the safety of the transport is assigned a higher value. The most relevant data may be data that is shown on a display at any time. In one embodiment, the most relevant data is shown more prominent on the display. In one embodiment, the most relevant data pertains to data that is received from an external source, such as a server and/or database communicably coupled to the transport such as through a network. The server may contain data related to an environment of the transport, such as traffic data, weather data such as weather patterns, and the like. This data may include one or more of the following non-inclusive list: upcoming deadlocked traffic, a dangerous weather pattern that is upcoming, a current speed, an alteration in an upcoming portion of a road, an upcoming dangerous intersection. Occupant(s) 116 are people that are in the transport and may include the driver and passengers in the transport.

The most relevant data is sent 120 to the display 110 via a message, such as a most relevant data message. This message is sent from the transport processor 114. In one embodiment, the message 120 contains additional data, related to the display of the data on the display 110. The additional data may include the following non-inclusive list: a percentage of the display 110 that the message 120 should take, the color of the data of the message 120, the characteristics of the data of the message 120 (such as the font, the font size, the font characteristics such as blinking, bold, italics, etc., and the like. In another embodiment, the message 120 contains a value (such as the value of the significance of the data previously determined), and the code in a processor in the display 110 contains logic that determines how to display the message 120 data according to the received significance value. In another embodiment, the message 120 contains bits that reflect whether the data is critical and/or safety-related and the display responds by altering the display of the data in a predefined manner.

In one embodiment, the software executing in the processor associated with the display 110 determines that if the data in the message 120 is critical and/or safety-related, then the data gains prominence on the display, such as the displayed data is enlarged in size, the font characteristics are modified (such as the font color, size, blinking capability, etc.). The processor in the display 110 executes code that displays the message 120 according to the logic therein. In another embodiment, the displaying of the data on the display 110 occurs by logic in the current application executing on the transport processor 114.

Occupants(s) 116 in the transport observe 122 the most relevant data 120 on the display 110. Sensors 112 in the transport observer the reaction 124, such as by cameras, radar, or the like where reaction data is sent 126 to the transport processor 114. In one embodiment, the data from the sensors 112 include images and/or video and/or the like, wherein the data is analyzed by the current application executing on a processor, such as the transport processor 114. The current application executing on a processor, such as the transport processor 114, determines if the level of the reaction is greater than a threshold 128. If no, then the process ends 130. If the level of the reaction is greater than a threshold, then data is sent to the display, such as in a notification message 132, wherein the data is displayed. The occupants view the data on the display 134. In one embodiment, the threshold may be determined by an entity, such as the manufacturer, and may be hardcoded into software executing the current application, for example. the current application detects characteristics from occupants, such as the occupant's reaction to the received data 120, in the transport from the received data 126 using functionality common in the art, such as object detection where an object can be determined as well as characteristics of the object such as an amount of tension related to a grip of an object such as a steering wheel, an amount of attention an occupant is placing on the road such as through the movement of the occupant's eyes and/or body position, a level of sound in the cabin of the transport, an indication of increased blood pressure wherein the increase is determined by the current application analyzing data from a sensor 112 such as a camera, etc. The current application determines a level of the reaction by comparing the analyzed data to a separate data, such as reaction data previously recorded, in one embodiment, to obtain a level of the reaction.

In one embodiment, the current application may perform an action of the transport, such as one or more of a next exit be taken by the transport, and that the transport pulls off of the road, such as on a shoulder of the road. This action may occur when either the level of the reaction of the at least one occupant is above a threshold and/or when the level of the reaction of the at least one occupant is not going down but rather increasing after modifications have been performed on the transport to lessen the reaction of the at least one occupant. The current application may send a message to a display 110 of the transport, wherein the message includes recommendations of an action recommendation. In another embodiment and when the transport is an autonomous vehicle, the current application may send a message to the transport processor 114, wherein the message includes the recommended action.

In one embodiment, other transports proximate the transport are affected by the transport. The effect of the other transports may be when both the transports are autonomous, one of the transports are autonomous or none of the transports are autonomous. Either in addition to or in place of sending a notification responsive to the determining of the reaction by the at least one occupant of the transport related to the most relevant data of the transport, the transport may communicate with one or more proximate transports where the communication allows one or more of a modification to a path of the one or more other transports, and an awareness of the scenario of the transport (such as a condition of the driver and/or occupant of the transport due to the reaction related to the most relevant data of the transport). In one embodiment, the transport may send a command that modifies the route of the other at least one transport, such as when the transport is needing to perform an exit and the other at least one transport is in a right lane. The message instructs the other at least one transport to either speed up or slows down to allow the transport to exit. The communication from the transport to the at least one other transport may be from a process of the transport such as the transport processor 114 and may utilize protocols commonly used in the art, such as Vehicle-to-Vehicle (V2V) communication. In one example, when the reaction is greater than a set threshold of an occupant in the transport, the transport processor 114 sends a message to at least one other proximate transport, such that the at least one other transport may be made aware of the situation in the transport. As an example, the message contains, “There is an occupant in the blue sedan next to you (license plate number XXG-364) that may be unwell, please drive with caution.”

In one embodiment, when a reaction from at least one occupant is determined by the system, modifications are made by the transport to lower the reaction of the at least one occupant. These modifications may include a modification of the music played in the cabin of the transport, such as the volume raised/lowered, and/or softer and more pleasing music being played through the speakers. The system may also modify the HVAC system. For example, the temperature can be raised or lowered to increase the comfort of the occupant, and/or the fan can be modified through the raising or lowering of the fan. In another example, the seat may be modified automatically, such as a raising or lowering of the seat, adjusting the lumbar cushion of the seat, the color of the lighting is altered to a calmer color such as sky blue, and/or adjusting the seatback.

In one embodiment, when the at least one occupant reenters the transport after modifications for that occupant have been performed by the transport in a previous occupation of the transport, the system 100 automatically detects the one or more occupants and performs the modifications one or more of before the one or more occupants enter the transport and when the one or more occupants are in the transport. The modifications performed by the transport one or more before the previous occupant reenters the transport, and just as the previous occupant reenters the transport may help the reaction of the occupant not rise to a previous reaction level. In one embodiment, the one or more occupants are detected by sensors 112 on the transport, such as radar, cameras, and the like located outside the transport and/or inside the transport. The data from the sensors 112 is sent to a processor associated with the transport, such as the transport processor 114. The current application executing in a processor associated with the transport, such as the transport processor 114 uses the received data from the sensors 112 to perform object detection where objects in the data are determined and the occupants are identified. The object detection and/or image processing software executing on the transport processor is used to verify the one or more occupants proximate the transport. After the one or more occupants are verified, the modifications are executed by the current application.

In one embodiment, when the level of a reaction of the at least one occupant is at a first reaction level, modifications are performed by the transport to lower the reaction. If after a period of time after the modification are performed by the transport the level of the reaction is above the first reaction level and/or the level of the reaction is not decreased but rather increased, then the current application executing on the transport, such as the transport processor 114, performs another event. This event may include one or more of sending a message to a display 110 wherein the event includes at least a description of the reaction of the at least one occupant and a description of the danger of the environment of the transport due to the severity of the reaction of the at least one occupant. In one embodiment, the current application may automatically alter the navigation destination of the transport to be an emergency facility when the level of the reaction exceeds a threshold.

In one embodiment, a condition affecting the reaction of the at least one occupant may decrease the safety of the transport. For example, assume the level of the reaction of the at least one occupant is 0. The condition of the at least one occupant is high blood pressure and an inability to walk on their own. The condition causes the threshold to be lowered, therefore accounting for the condition of the at least one occupant. The lowering of the threshold allows the current application to perform modifications in less stressful environments.

Figure 2A:
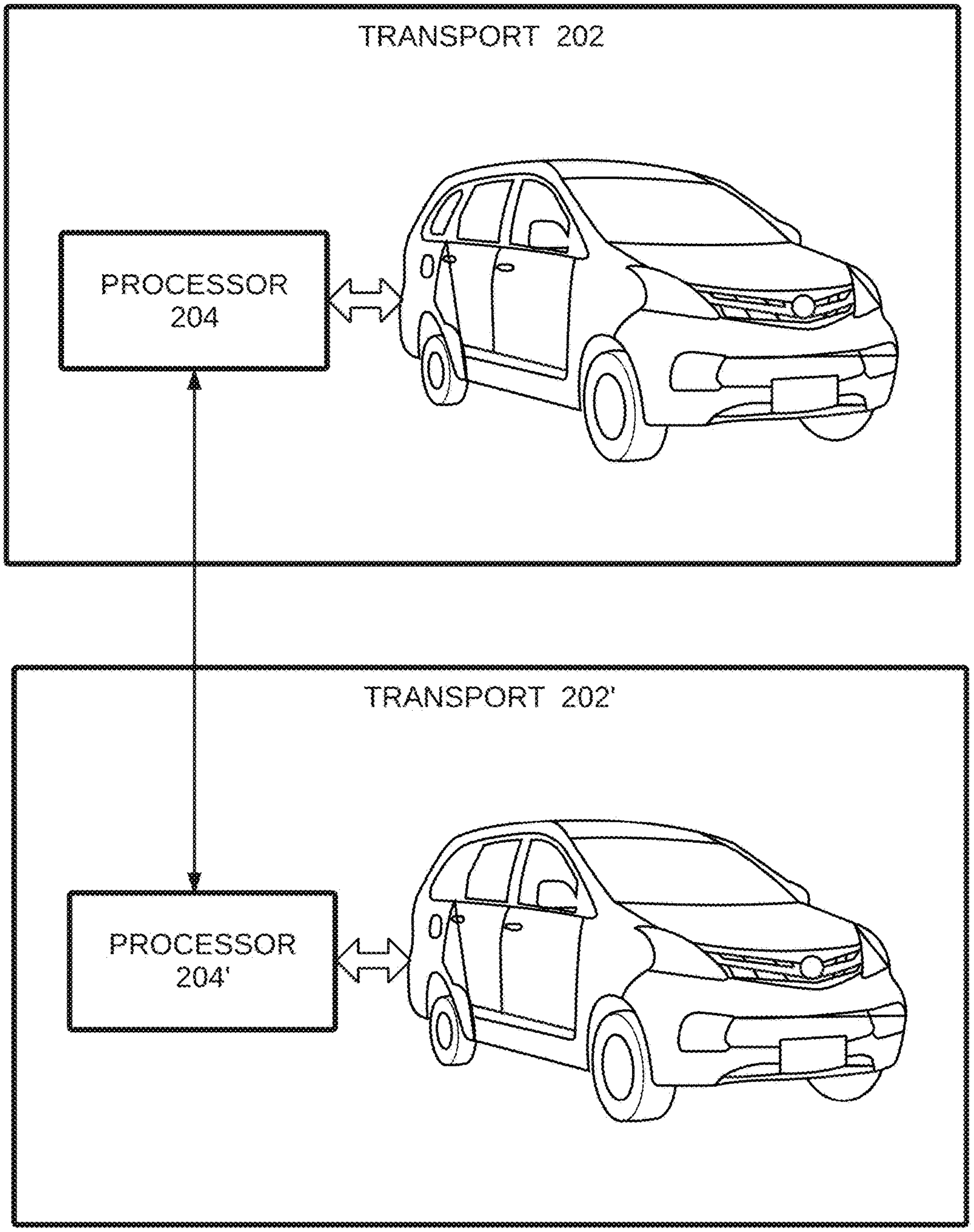
FIG. 2A illustrates a transport network diagram, according to example embodiments.

FIG. 2A illustrates a transport network diagram 200, according to example embodiments. The network comprises elements including a transport 202 including a processor 204, as well as a transport 202' including a processor 204'. The transports 202, 202' communicate with one another via the processors 204, 204', as well as other elements (not shown) including transceivers, transmitters, receivers, storage, sensors and other elements capable of providing communication. The communication between the transports 202, 202' can occur directly, via a private and/or a public network (not shown) or via other transports and elements comprising one or more of a processor, memory, and software. Although depicted as single transports and processors, a plurality of transports and processors may be present. One or more of the applications, features, steps, solutions, etc., described and/or depicted herein may be utilized and/or provided by the instant elements.

Figure 2B:
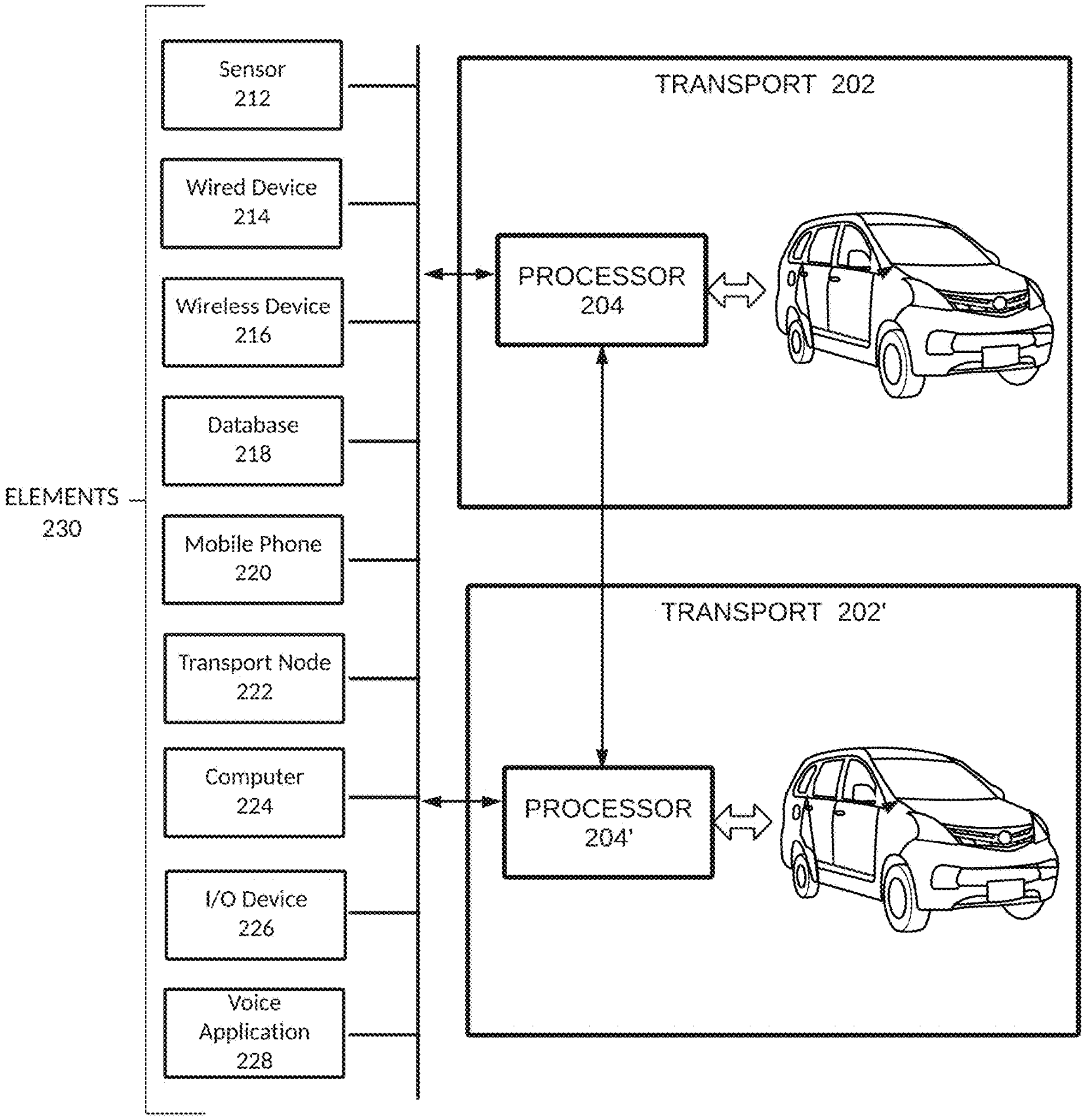
FIG. 2B illustrates another transport network diagram, according to example embodiments.

FIG. 2B illustrates another transport network diagram 210, according to example embodiments. The network comprises elements including a transport 202 including a processor 204, as well as a transport 202' including a processor 204'. The transports 202, 202' communicate with one another via the processors 204, 204', as well as other elements (not shown) including transceivers, transmitters, receivers, storage, sensors and other elements capable of providing communication. The communication between the transports 202, 202' can occur directly, via a private and/or a public network (not shown) or via other transports and elements comprising one or more of a processor, memory, and software. The processors 204, 204' can further communicate with one or more elements 230 including sensor 212, wired device 214, wireless device 216, database 218, mobile phone 220, transport 222, computer 224, I/O device 226 and voice application 228. The processors 204, 204' can further communicate with elements comprising one or more of a processor, memory, and software.

Although depicted as single transports, processors and elements, a plurality of transports, processors and elements may be present. Information or communication can occur to and/or from any of the processors 204, 204' and elements 230. For example, the mobile phone 220 may provide information to the processor 204, which may initiate the transport 202 to take an action, may further provide the information or additional information to the processor 204', which may initiate the transport 202' to take an action, may further provide the information or additional information to the mobile phone 220, the transport 222, and/or the computer 224. One or more of the applications, features, steps, solutions, etc., described and/or depicted herein may be utilized and/or provided by the instant elements.

Figure 2C:
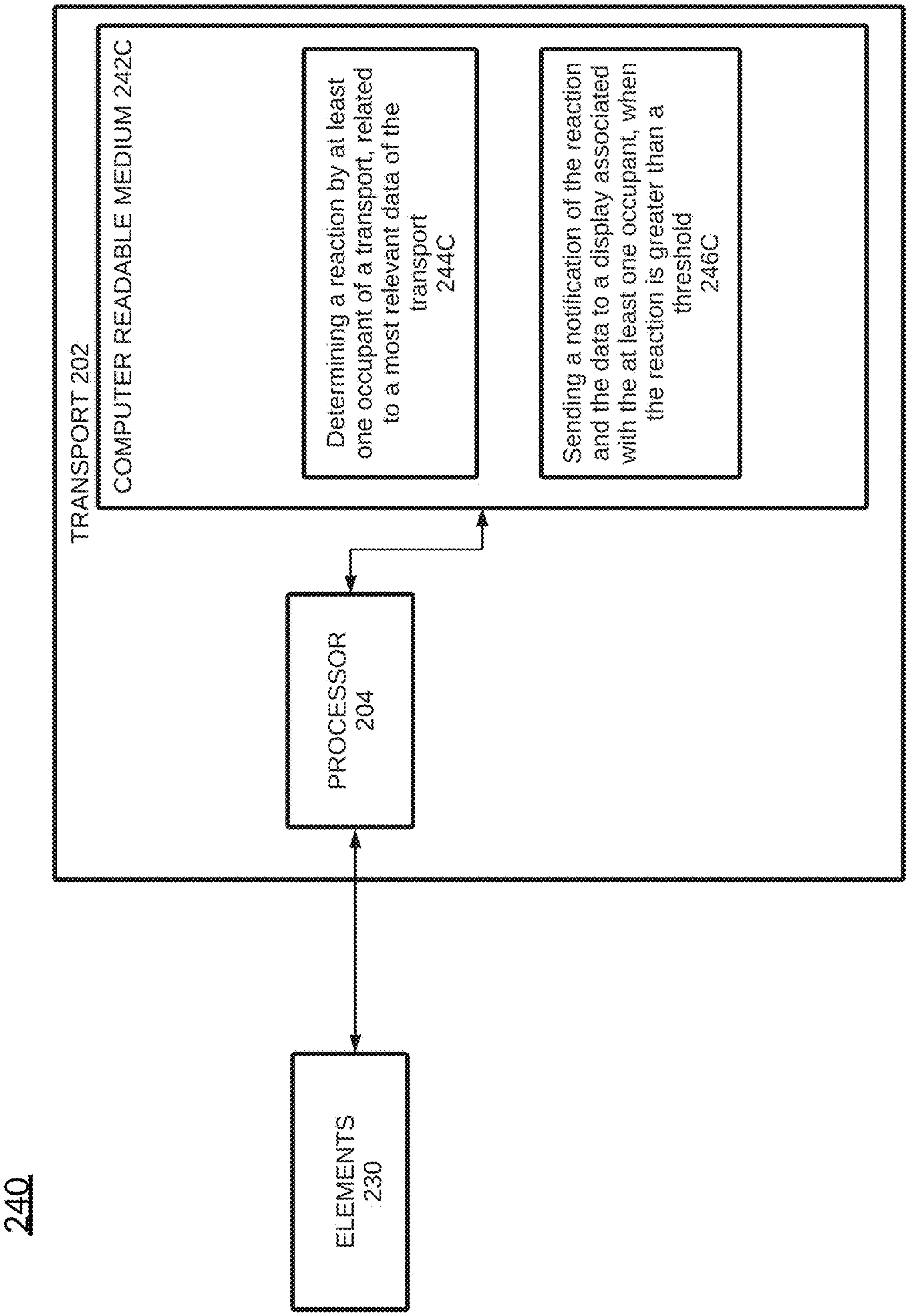
FIG. 2C illustrates yet another transport network diagram, according to example embodiments.

FIG. 2C illustrates yet another transport network diagram 240, according to example embodiments. The network comprises elements including a transport 202 including a processor 204 and a non-transitory computer readable medium 242C. The processor 204 is communicably coupled to the computer readable medium 242C and elements 230 (which were depicted in FIG. 2B). The transport 202 could be a transport, server or any device which includes a processor and memory.

The processor 204 performs one or more of determining a reaction by at least one occupant of a transport, related to a most relevant data of the transport 244C, and sending a notification of the reaction and the data to a display associated with the at least one occupant, when the reaction is greater than a threshold 246C.

Figure 2D:
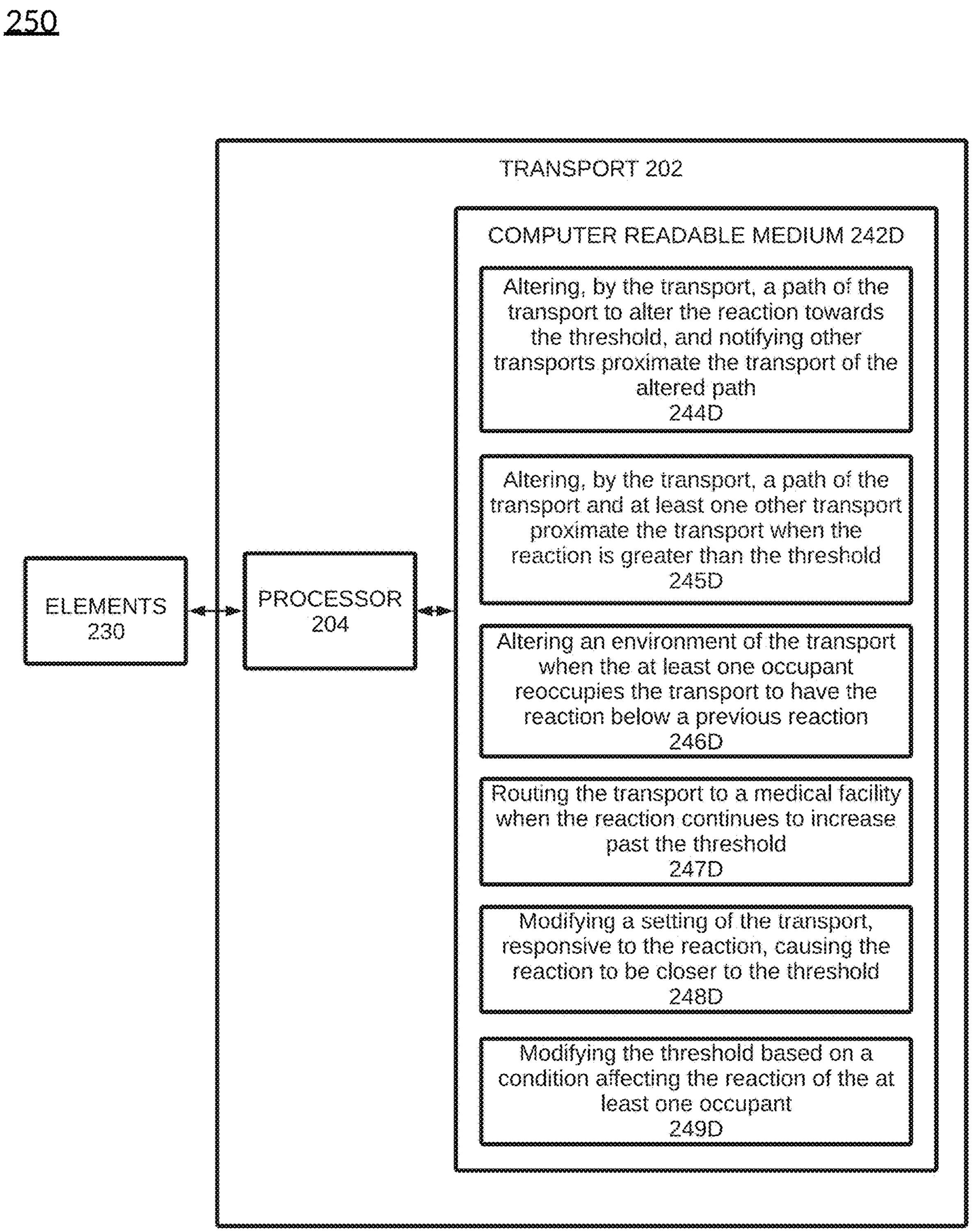
FIG. 2D illustrates a further transport network diagram, according to example embodiments.

FIG. 2D illustrates a further transport network diagram 250, according to example embodiments. The network comprises elements including a transport 202 including a processor 204 and a non-transitory computer readable medium 242D. The processor 204 is communicably coupled to the computer readable medium 242D and elements 230 (which were depicted in FIG. 2B). The transport 202 could be a transport, server or any device which includes a processor and memory.

The processor 204 performs one or more of altering, by the transport, a path of the transport to alter the reaction towards the threshold, and notifying other transports proximate the transport of the altered path 244D, altering, by the transport, a path of the transport and at least one other transport proximate the transport when the reaction is greater than the threshold 245D, altering an environment of the transport when the at least one occupant reoccupies the transport to have the reaction below a previous reaction 246D, routing the transport to a medical facility when the reaction continues to increase past the threshold 247D, modifying a setting of the transport, responsive to the reaction, causing the reaction to be closer to the threshold 248D, and modifying the threshold based on a condition affecting the reaction of the at least one occupant 249D.

Figure 2E:
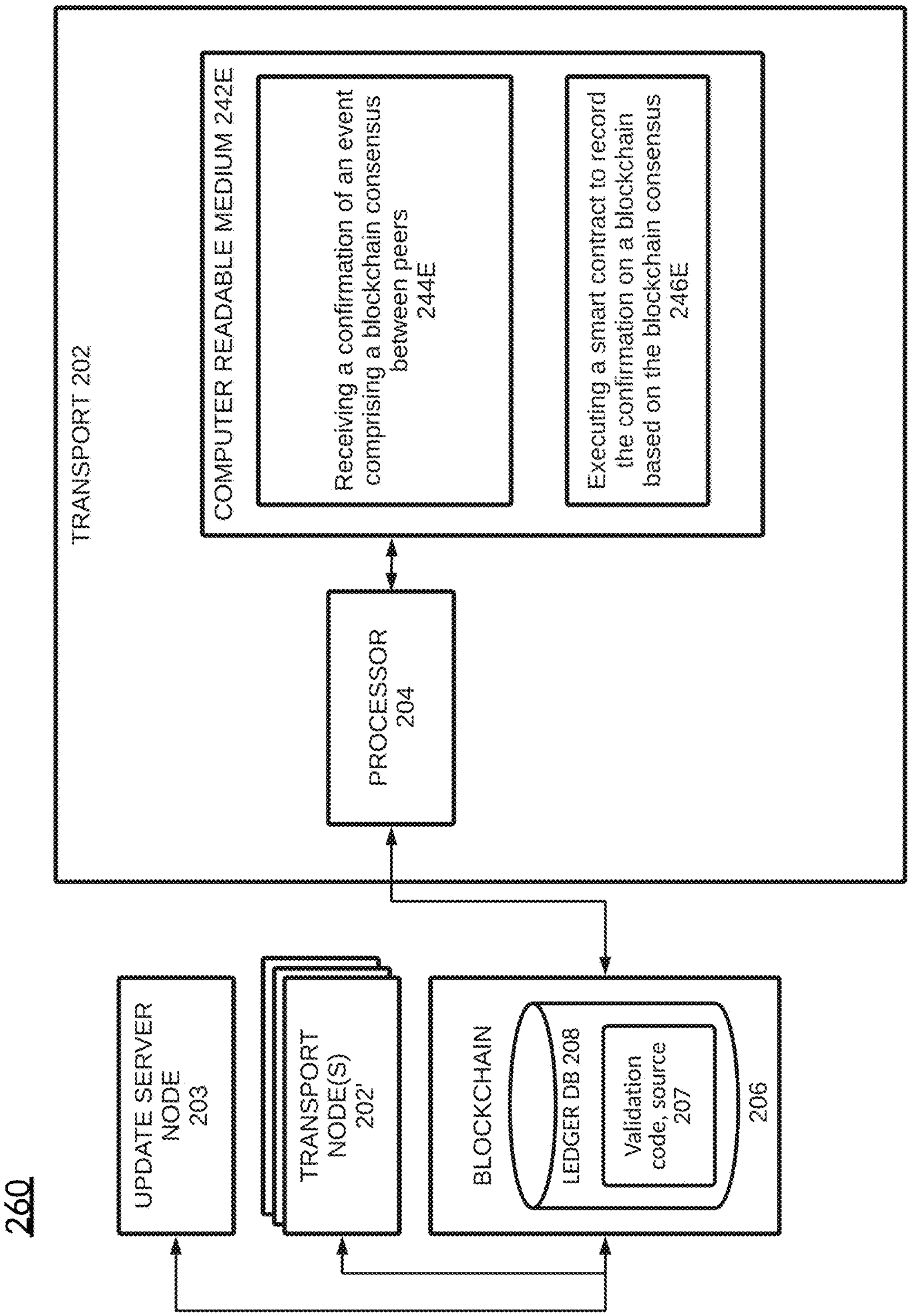
FIG. 2E illustrates yet a further transport network diagram, according to example embodiments.

FIG. 2E illustrates yet a further transport network diagram 260, according to example embodiments. Referring to FIG. 2E, the network diagram 260 includes a transport 202 connected to other transports 202' and to an update server node 203 over a blockchain network 206. The transports 202 and 202' may represent transports/vehicles. The blockchain network 206 may have a ledger 208 for storing software update validation data and a source 207 of the validation for future use (e.g., for an audit).

While this example describes in detail only one transport 202, multiple such nodes may be connected to the blockchain 206. It should be understood that the transport 202 may include additional components and that some of the components described herein may be removed and/or modified without departing from a scope of the instant application. The transport 202 may have a computing device or a server computer, or the like, and may include a processor 204, which may be a semiconductor-based microprocessor, a central processing unit (CPU), an application specific integrated circuit (ASIC), a field-programmable gate array (FPGA), and/or another hardware device. Although a single processor 204 is depicted, it should be understood that the transport 202 may include multiple processors, multiple cores, or the like, without departing from the scope of the instant application. The transport 202 could be a transport, server or any device which includes a processor and memory.

The processor 204 performs one or more of receiving a confirmation of an event from one or more elements described or depicted herein, wherein the confirmation comprises a blockchain consensus between peers represented by any of the elements 244E, and executing a smart contract to record the confirmation on a blockchain based on the blockchain consensus 246E. Consensus is formed between one or more of any element 230 and/or any element described or depicted herein including a transport, a server, a wireless device, etc. In another embodiment, the transport 202 can be one or more of any element 230 and/or any element described or depicted herein including a server, a wireless device, etc.

The processors and/or computer readable medium 242E may fully or partially reside in the interior or exterior of the transports. The steps or features stored in the computer readable medium 242E may be fully or partially performed by any of the processors and/or elements in any order. Additionally, one or more steps or features may be added, omitted, combined, performed at a later time, etc.

Figure 2F:
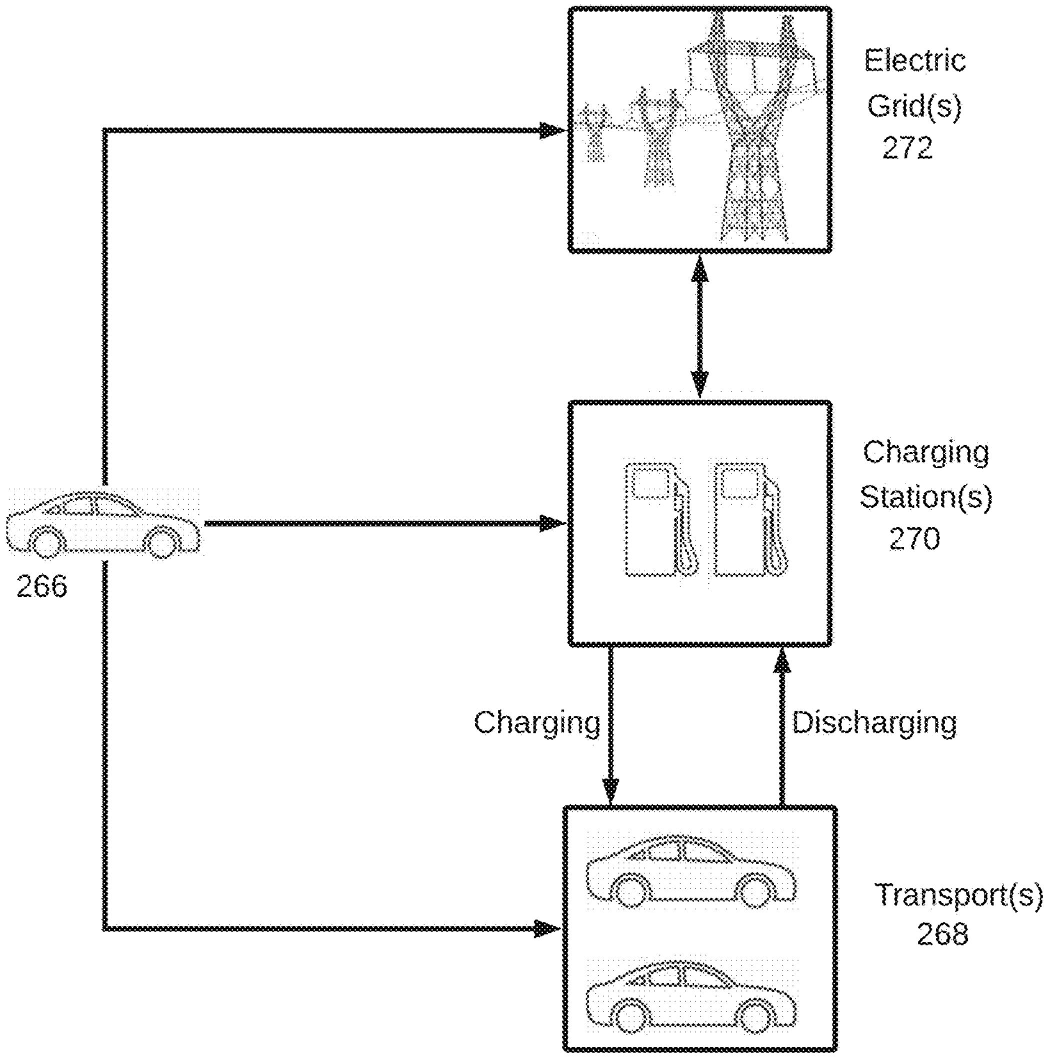
FIG. 2F illustrates a diagram depicting electrification of one or more elements, according to example embodiments.

FIG. 2F illustrates a diagram 265 depicting electrification of one or more elements. In one embodiment, a transport 266 may provide power stored in its batteries to one or more elements including other transport(s) 268, charging station(s) 270 and electric grid(s) 272. The electric grid(s) 272 is/are coupled to one or more of the charging stations 270 which may be coupled to one or more of the transports 268. This configuration allows distribution of electricity/power received from the transport 266. The transport 266 may also interact with the other transport(s) 268, such as via Vehicle to Vehicle (V2V) technology, communication over cellular, WiFi, and the like. The transport 266 may also interact wirelessly and/or in a wired manner with other transports 268, the charging station(s) 270 and/or with the electric grid(s) 272. In one embodiment, the transport 266 is routed (or routes itself) in a safe and efficient manner to the electric grid(s) 272, the charging station(s) 270, or the other transport(s) 268. Using one or more embodiments of the instant solution, the transport 266 can provide energy to one or more of the elements depicted herein in a variety of advantageous ways as described and/or depicted herein. Further, the safety and efficiency of the transport may be increased, and the environment may be positively affected as described and/or depicted herein.

The term 'energy' may be used to denote any form of energy received, stored, used, shared and/or lost by the transport(s). The energy may be referred to in conjunction with a voltage source and/or a current supply of charge provided from an entity to the transport(s) during a charge/use operation. Energy may also be in the form of fossil fuels (for example, for use with a hybrid transport) or via alternative power sources, including but not limited to lithium based, nickel based, hydrogen fuel cells, atomic/nuclear energy, fusion based energy sources, and energy generated on-the-fly during an energy sharing and/or usage operation for increasing or decreasing one or more transports energy levels at a given time.

In one embodiment, the charging station 270 manages the amount of energy transferred from the transport 266 such that there is sufficient charge remaining in the transport 266 to arrive at a destination. In one embodiment, a wireless connection is used to wirelessly direct an amount of energy transfer between transports 268, wherein the transports may both be in motion. In one embodiment, an idle vehicle, such as a vehicle 266 (which may be autonomous) is directed to provide an amount of energy to a charging station 270 and return to the original location (for example, its original location or a different destination). In one embodiment, a mobile energy storage unit (not shown) is used to collect surplus energy from at least one other transport 268 and transfer the stored, surplus energy at a charging station 270. In one embodiment, factors determine an amount of energy to transfer to a charging station 270, such as distance, time, as well as traffic conditions, road conditions, environmental/weather conditions, the vehicle's condition (weight, etc.), an occupant(s) schedule while utilizing the vehicle, a prospective occupant(s) schedule waiting for the vehicle, etc. In one embodiment, the transport(s) 268, the charging station(s) 270 and/or the electric grid(s) 272 can provide energy to the transport 266.

In one embodiment, a location such as a building, a residence or the like, (not depicted), communicably coupled to one or more of the electric grid 272, the transport 266, and/or the charging station(s) 270. The rate of electric flow to one or more of the location, the transport 266, the other transport(s) 268 is modified, depending on external conditions, such as weather. For example, when the external temperature is extremely hot or extremely cold, raising the chance for an outage of electricity, the flow of electricity to a connected vehicle 266/268 is slowed to help minimize the chance for an outage.

In one embodiment, the solutions described and depicted herein can be utilized to determine load effects on the transport and/or the system, to provide energy to the transport and/or the system based on future needs and/or priorities, and provide intelligence between an apparatus containing a module and a vehicle allowing the processor of the apparatus to wirelessly communicate with a vehicle regarding an amount of energy store in a battery on the vehicle. In one embodiment, the solutions can also be utilized to provide charge to a location from a transport based on factors such as the temperature at the location, the cost of the energy and the power level at the location. In one embodiment, the solutions can also be utilized to manage an amount of energy remaining in a transport after a portion of charge has been transferred to a charging station. In one embodiment, the solutions can also be utilized to notify a vehicle to provide an amount of energy from batteries on the transport wherein the amount of energy to transfer is based on the distance of the transport to a module to receive the energy.

In one embodiment, the solutions can also be utilized to use a mobile energy storage unit that uses a determined path to travel to transports that have excess energy and deposit the stored energy into the electric grid. In one embodiment, the solutions can also be utilized to determine a priority of the transport's determination of the need to provide energy to grid, and the priority of a current need of the transport, such as the priority of a passenger, or upcoming passenger, or current cargo, or upcoming cargo. In one embodiment, the solutions can also be utilized to determine that when a vehicle is idle, the vehicle decides to maneuver to a location to discharge excess energy to the energy grid, then return to the previous location. In one embodiment, the solutions can also be utilized to determine an amount of energy needed by a transport to provide another transport with needed energy via transport to transport energy transfer based on one or more conditions such as weather, traffic, road conditions, car conditions, and occupants and/or goods in another transport, and instruct the transport to route to another transport and provide the energy. In one embodiment, the solutions can also be utilized to transfer energy from one vehicle in motion to another vehicle in motion. In one embodiment, the solutions can also be utilized to retrieve energy by a transport based on an expended energy by the transport to reach a meeting location with another transport, provide a service, and an estimated expended energy to return to an original location. In one embodiment, the solutions can also be utilized to provide a remaining distance needed to a charging station, and the charging station to determine an amount of energy to be retrieved from the transport wherein the amount of charge remaining is based on the remaining distance. In one embodiment, the solutions can also be utilized to manage a transport that is concurrently charged by more than one point at the same time, such as both a charging station via a wired connection and another transport via a wireless connection. In one embodiment, the solutions can also be utilized to apply a priority to the dispensing of energy to transports wherein a priority is given to those transports that will provide a portion of their stored charge to another entity such as an electric grid, a residence, and the like. Further, the instant solution as described and depicted with respect to FIG. 2F can be utilized in this and other networks and/or systems.

Figure 2G:
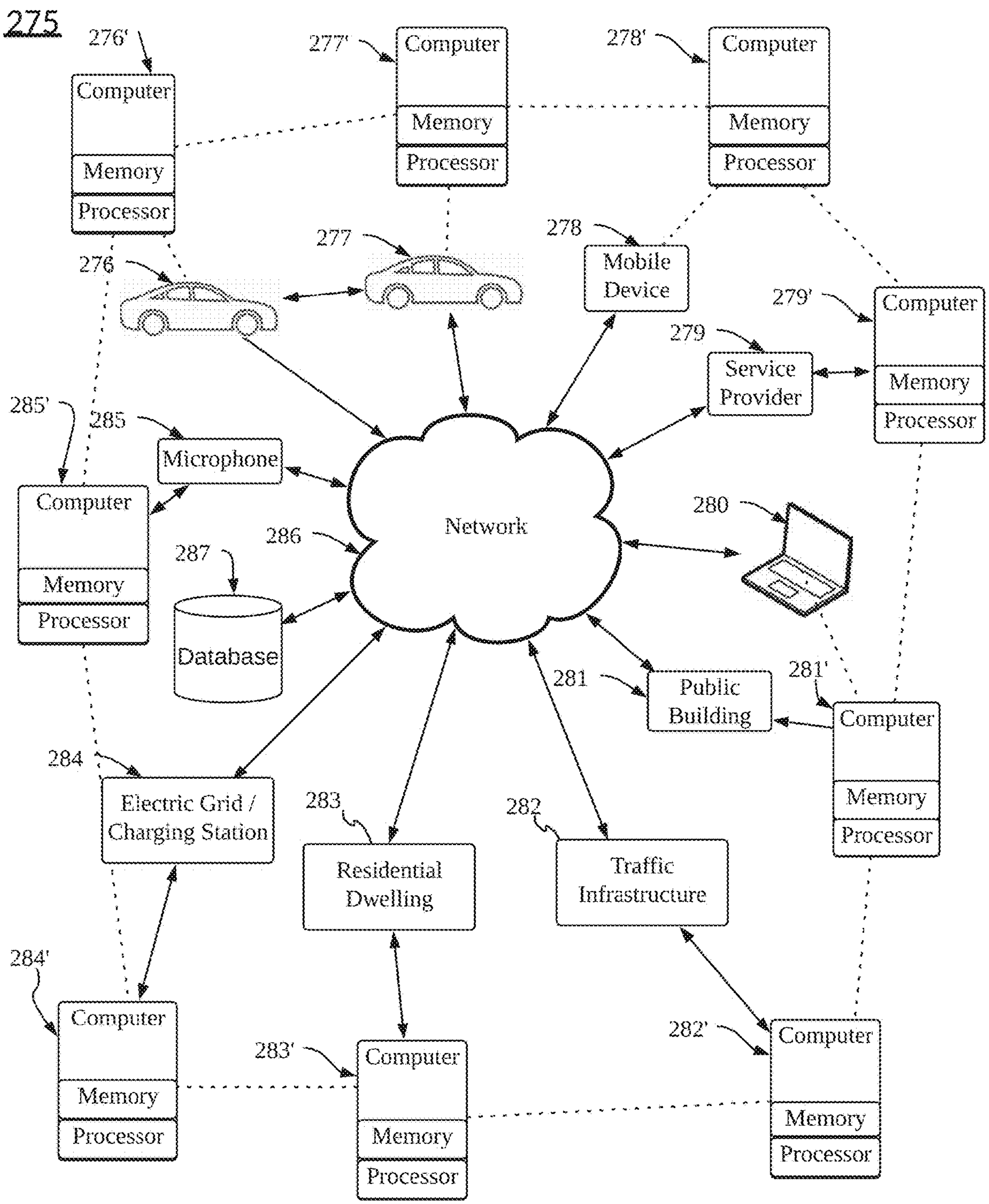
FIG. 2G illustrates a diagram depicting interconnections between different elements, according to example embodiments.

FIG. 2G is a diagram showing interconnections between different elements 275. The instant solution may be stored and/or executed entirely or partially on and/or by one or more computing devices 278', 279', 281', 282', 283', 284', 276', 285', 287' and 277' associated with various entities, all communicably coupled and in communication with a network 286. A database 287 is communicably coupled to the network and allows for the storage and retrieval of data. In one embodiment, the database is an immutable ledger. One or more of the various entities may be a transport 276, one or more service provider 279, one or more public buildings 281, one or more traffic infrastructure 282, one or more residential dwellings 283, an electric grid/charging station 284, a microphone 285, and/or another transport 277. Other entities and/or devices, such as one or more private users using a smartphone 278, a laptop 280, an augmented reality (AR) device, a virtual reality (VR) device, and/or any wearable device may also interwork with the instant solution. The smartphone 278, laptop 280, the microphone 285, and other devices may be connected to one or more of the connected computing devices 278', 279', 281', 282', 283', 284', 276', 285', 287', and 277'. The one or more public buildings 281 may include various agencies. The one or more public buildings 281 may utilize a computing device 281'. The one or more service provider 279 may include a dealership, a tow truck service, a collision center or other repair shop. The one or more service provider 279 may utilize a computing apparatus 279'. These various computer devices may be directly and/or communicably coupled to one another such as via wired networks, wireless networks, blockchain networks, and the like. The microphone 285 may be utilized as a virtual assistant, in one embodiment. In one embodiment, the one or more traffic infrastructure 282 may include one or more traffic signals, one or more sensors including one or more cameras, vehicle speed sensors or traffic sensors, and/or other traffic infrastructure. The one or more traffic infrastructure 282 may utilize a computing device 282'.

In one embodiment, a transport 277/276 is capable of transporting a person, an object, a permanently or temporarily affixed apparatus, and the like. In one embodiment, the transport 277 may communicate with transport 276 via V2V communication, through the computers associated with each transport 276' and 277' and may be referred to as a transport, car, vehicle, automobile, and the like. The transport 276/277 may be a self-propelled wheeled conveyance, such as a car, a sports utility vehicle, a truck, a bus, a van, or other motor or battery-driven or fuel cell-driven transport. For example, transport 276/277 may be an electric vehicle, a hybrid vehicle, a hydrogen fuel cell vehicle, a plug-in hybrid vehicle, or any other type of vehicle that has a fuel cell stack, a motor, and/or a generator. Other examples of vehicles include bicycles, scooters, trains, planes, or boats, and any other form of conveyance that is capable of transportation. The transport 276/277 may be semi-autonomous or autonomous. For example, transport 276/277 may be self-maneuvering and navigate without human input. An autonomous vehicle may have and use one or more sensors and/or a navigation unit to drive autonomously.

In one embodiment, the solutions described and depicted herein can be utilized to determine an access to a transport via consensus of blockchain. In one embodiment, the solutions can also be utilized to perform profile validation before allowing an occupant to use a transport. In one embodiment, the solutions can also be utilized to have the transport indicate (visually, but also verbally in another embodiment, etc.) on or from the transport for an action the user needs to perform (that could be pre-recorded) and verify that it is the correct action. In one embodiment, the solutions can also be utilized to provide an ability to for a transport to determine, based on the risk level associated with data and driving environment, how to bifurcate the data and distribute a portion of the bifurcated data, with a lower risk level during a safe driving environment, to the occupant, and later distributing a remaining portion of the bifurcated data, with a higher risk level, to the occupant after the occupant has departed the transport. In one embodiment, the solutions can also be utilized to handle the transfer of a vehicle across boundaries (such as a country/state/etc.) through the use of blockchain and/or smart contracts and apply the rules of the new area to the vehicle.

In one embodiment, the solutions can also be utilized to allow a transport to continue to operate outside a boundary when a consensus is reached by the transport based on the operation of the transport and characteristics of an occupant of the transport. In one embodiment, the solutions can also be utilized to analyze the available data upload/download speed of a transport, size of the file and speed/direction the transport is traveling, to determine the distance needed to complete a data upload/download and assign a secure area boundary for the data upload/download to be executed. In one embodiment, the solutions can also be utilized to perform a normally dangerous maneuver in a safe manner, such as when the system determines that an exit is upcoming and when the transport is seemingly not prepared to exit (e.g. in the incorrect lane or traveling at a speed that is not conducive to making the upcoming exit) and instruct the subject transport as well as other proximate transports to allow the subject transport to exit in a safe manner. In one embodiment, the solutions can also be utilized to use one or more vehicles to validate diagnostics of another transport while both the one or more vehicles and the other transport are in motion.

In one embodiment, the solutions can also be utilized to detect lane usage at a location and time of day to either inform an occupant of a transport or direct the transport to recommend or not recommend a lane change. In one embodiment, the solutions can also be utilized to eliminate the need to send information through the mail and the need for a driver/occupant to respond by making a payment through the mail or in person. In one embodiment, the solutions can also be utilized to provide a service to an occupant of a transport, wherein the service provided is based on a subscription, and wherein the permission is acquired from other transports connected to the profile of the occupant. In one embodiment, the solutions can also be utilized to record changes in the condition of a rented object. In one embodiment, the solutions can also be utilized to seek a blockchain consensus from other transports that are in proximity to a damaged transport. In one embodiment, the solutions can also be utilized to receive media, from a server such as an insurance entity server, from the transport computer, which may be related to an accident. The server accesses one or more media files to access the damage to the transport and stores the damage assessment onto a blockchain. In one embodiment, the solutions can also be utilized to obtain a consensus to determine the severity of an event from a number of devices over various times prior to the event related to a transport.

In one embodiment, the solutions can also be utilized to solve a problem with a lack of video evidence for transport-related accidents. The current solution details the querying of media, by the transport involved in the accident, related to the accident from other transports that may have been proximate to the accident. In one embodiment, the solutions can also be utilized to utilize transports and other devices (for example, a pedestrian's cell phone, a streetlight camera, etc.) to record specific portions of a damaged transport.

In one embodiment, the solutions can also be utilized to warn an occupant when a transport is navigating toward a dangerous area and/or event, allowing for a transport to notify occupants or a central controller of a potentially dangerous area on or near the current transport route. In one embodiment, the solutions can also be utilized to detect when a transport traveling at a high rate of speed, at least one other transport is used to assist in slowing down the transport in a manner that minimally affects traffic. In one embodiment, the solutions can also be utilized to identify a dangerous driving situation where media is captured by the vehicle involved in the dangerous driving situation. A geofence is established based on the distance of the dangerous driving situation, and additional media is captured by at least one other vehicle within the established geofence. In one embodiment, the solutions can also be utilized to send a notification to one or more occupants of a transport that that transport is approaching a traffic control marking on a road, then if a transport crosses a marking, receiving indications of poor driving from other, nearby transports. In one embodiment, the solutions can also be utilized to make a transport partially inoperable by (in certain embodiments), limiting speed, limiting the ability to be near another vehicle, limiting speed to a maximum, and allowing only a given number of miles allowed per time period.

In one embodiment, the solutions can also be utilized to overcome a need for reliance on software updates to correct issues with a transport when the transport is not being operated correctly. Through the observation of other transports on a route, a server will receive data from potentially multiple other transports observing an unsafe or incorrect operation of a transport. Through analysis, these observations may result in a notification to the transport when the data suggest an unsafe or incorrect operation. In one embodiment, the solutions can also be utilized to provide notification between a transport and a potentially dangerous situation involving a person external to the transport. In one embodiment, the solutions can also be utilized to send data to a server by devices either associated with an accident with a transport, or devices proximate to the accident. Based on the severity of the accident or near accident, the server notifies the senders of the data. In one embodiment, the solutions can also be utilized to provide recommendations for operating a transport to either a driver or occupant of a transport based on the analysis of data. In one embodiment, the solutions can also be utilized to establish a geo-fence associated with a physical structure and determining payment responsibility to the transport. In one embodiment, the solutions can also be utilized to coordinate the ability to drop off a vehicle at a location using both the current state at the location, and a proposed future state using navigation destinations of other vehicles. In one embodiment, the solutions can also be utilized to coordinate the ability to automatically arrange for the drop off of a vehicle at a location such as a transport rental entity.

In one embodiment, the solutions can also be utilized to move transport to another location based on a user's event. More particularly, the system tracks a user's device, and modifies the transport to be moved proximate to the user upon the conclusion of the original event, or a modified event. In one embodiment, the solutions can also be utilized to allow for the validation of available locations within an area through the existing transports within the area. The approximate time when a location may be vacated is also determined based on verifications from the existing transports. In one embodiment, the solutions can also be utilized to move a transport to closer parking spaces as one becomes available and the elapsed time since initially parking is less than the average time of the event. Furthermore, moving the transport to a final parking space when the event is completed or according to a location of a device associated with at least one occupant of the transport. In one embodiment, the solutions can also be utilized to plan for the parking prior to the upcoming crowd. The system interacts with the transport to offer some services at a less than full price and/or guide the transport to alternative parking locations based on a priority of the transport, increasing optimization of the parking situation before arriving.

In one embodiment, the solutions can also be utilized to sell fractional ownership in transports or in determining pricing and availability in ride-sharing applications. In one embodiment, the solutions can also be utilized to provide accurate and timely reports of dealership sales activities well beyond what is currently available. In one embodiment, the solutions can also be utilized to allow a dealership to request an asset over the blockchain. By using the blockchain, a consensus is obtained before any asset is moved. Additionally, the process is automated, and payment may be initiated over the blockchain. In one embodiment, the solutions can also be utilized to arrange agreements that are made with multiple entities (such as service centers) wherein a consensus is acquired, and an action performed (such as diagnostics). In one embodiment, the solutions can also be utilized to associate digital keys with multiple users. A first user may be the operator of the transport, and a second user is the responsible party for the transport. These keys are authorized by a server where the proximity of the keys are validated against the location of a service provider. In one embodiment, the solutions can also be utilized to determine a needed service on a transport destination. One or more service locations are located that are able to provide the needed service that is both within an area on route to the destination and has availability to perform the service. The navigation of the transport is updated with the determined service location. A smart contract is identified that contains a compensation value for the service, and a blockchain transaction is stored in a distributed ledger for the transaction.

In one embodiment, the solutions can also be utilized to interfacing a service provider transport with a profile of an occupant of a transport to determine services and goods which may be of interest to occupants in a transport. These services and goods are determined by an occupant's history and/or preferences. The transport then receives offers from the service provider transport and, in another embodiment, meets the transport to provide the service/good. In one embodiment, the solutions can also be utilized to detect a transport within a range and send a service offer to the transport (such as a maintenance offer, a product offer, or the like). An agreement is made between the system and the transport, and a service provider is selected by the system to provide the agreement. In one embodiment, the solutions can also be utilized to assign one or more transports as a roadway manager, where the roadway manager assists in the control of traffic. The roadway manager may generate a roadway indicator (such as lights, displays, sounds) to assist in the flow of traffic. In one embodiment, the solutions can also be utilized to alert a driver of a transport by a device, wherein the device may be the traffic light or near an intersection. The alert is sent upon an event, such as when a light turns green and the transport in the front of a list of transports does not move.

Figure 2H:
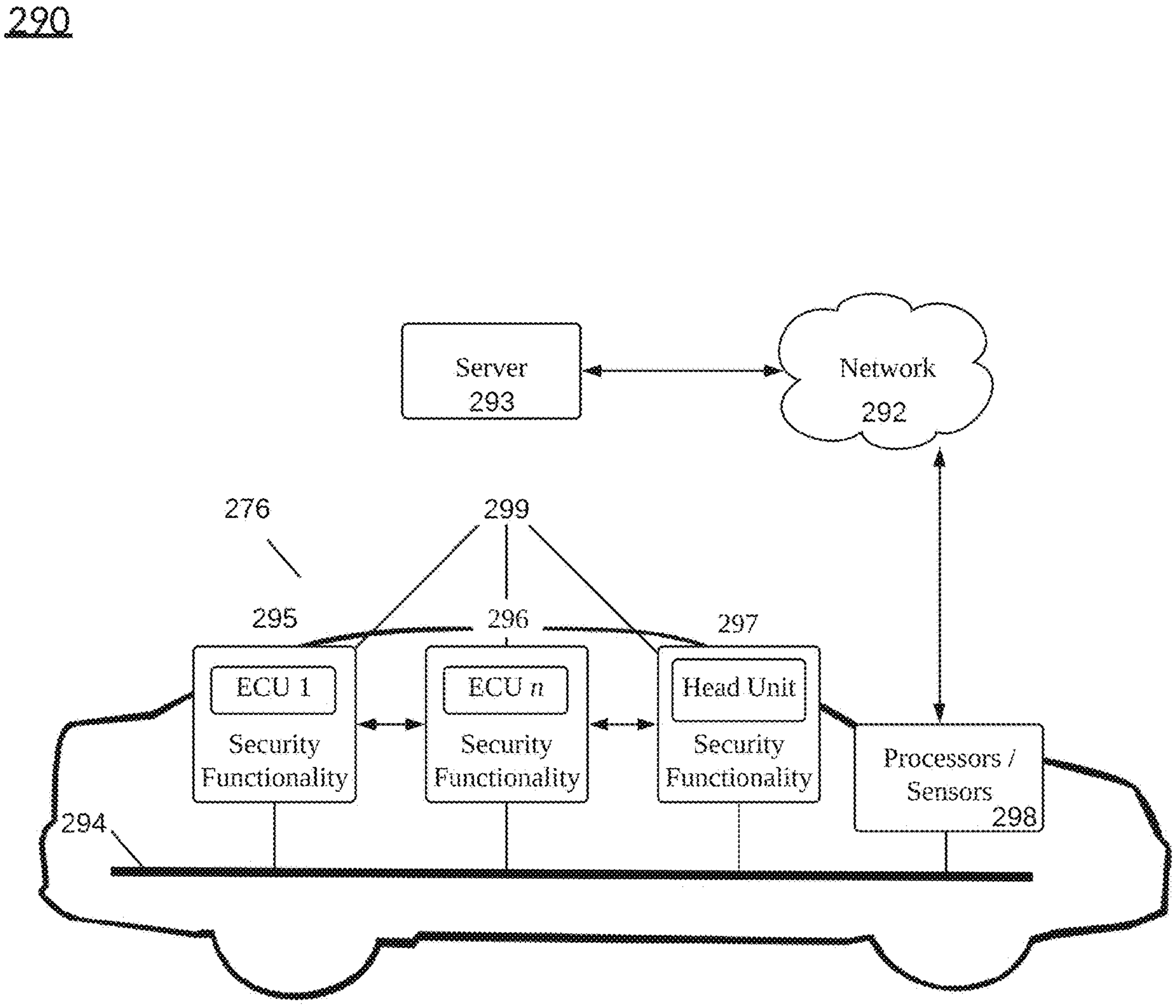
FIG. 2H illustrates a further diagram depicting interconnections between different elements, according to example embodiments.

FIG. 2H is another block diagram showing interconnections between different elements in one example 290. A transport 276 is presented and includes ECUs 295, 296, and a Head Unit (otherwise known as an Infotainment System) 297. An Electrical Control Unit (ECU) is an embedded system in automotive electronics controlling one or more of the electrical systems or subsystems in a transport. ECUs may include but are not limited to the management of a transport's engine, brake system, gearbox system, door locks, dashboard, airbag system, infotainment system, electronic differential, and active suspension. ECUs are connected to the transport's Controller Area Network (CAN) bus 294. The ECUs may also communicate with a transport computer 298 via the CAN bus 294. The transport's processors/sensors (such as the transport computer) 298 can communicate with external elements, such as a server 293 via a network 292 (such as the Internet). Each ECU 295, 296 and Head Unit 297 may contain its own security policy. The security policy defines permissible processes that are able to be executed in the proper context. In one embodiment, the security policy may be partially or entirely provided in the transport computer 298.

ECUs 295, 296 and Head Unit 297 may each include a custom security functionality element 299 defining authorized processes and contexts within which those processes are permitted to run. Context-based authorization to determine validity if a process is able to be executed allows ECUs to maintain secure operation and prevent unauthorized access from elements such as the transport's Controller Area Network (CAN Bus). When an ECU encounters a process that is unauthorized, that ECU can block the process from operating. Automotive ECUs can use different contexts to determine whether a process is operating within its permitted bounds, such as proximity contexts such as nearby objects, distance to approaching objects, speed, and trajectory relative to other moving objects, operational contexts such as an indication of whether the transport is moving or parked, the transport's current speed, the transmission state, user-related contexts such as devices connected to the transport via wireless protocols, use of the infotainment, cruise control, parking assist, driving assist, location-based contexts, and/or other contexts.

In one embodiment, the solutions described and depicted herein can be utilized to make a transport partially inoperable by (in certain embodiments), limiting speed, limiting the ability to be near another vehicle, limiting speed to a maximum, and allowing only a given numbers of miles allowed per time period. In one embodiment, the solutions can also be utilized to use a blockchain to facilitate exchange of vehicle possession wherein data is sent to a server by devices either associated with an accident with a transport, or devices proximate to the accident. Based on the severity of the accident or near accident, the server notifies the senders of the data. In one embodiment, the solutions can also be utilized to help the transport to avoid accidents, such as when the transport is involved in an accident by a server that queries other transports that are proximate to the accident. The server seeks to obtain data from the other transports, allowing the server to gain an understanding of the nature of the accident from multiple vantage points. In one embodiment, the solutions can also be utilized to determine that sounds from a transport are atypical and transmit data related to the sounds as well as a possible source location to a server wherein the server can determine possible causes and avoid a potentially dangerous situation. In one embodiment, the solutions can also be utilized to establish a location boundary via the system when a transport is involved in an accident. This boundary is based on decibels associated with the accident. Multimedia content for a device within the boundary is obtained to assist in further understanding the scenario of the accident. In one embodiment, the solutions can also be utilized to associate a vehicle with an accident, then capture media obtained by devices proximate to the location of the accident. The captured media is saved as a media segment. The media segment is sent to another computing device which builds a sound profile of the accident. This sound profile will assist in understanding more details surrounding the accident.

In one embodiment, the solutions can also be utilized to utilize sensors to record audio, video, motion, etc. to record an area where a potential event has occurred, such as if a transport comes in contact or may come in contact with another transport (while moving or parked), the system captures data from the sensors which may reside on one or more of the transports and/or on fixed or mobile objects. In one embodiment, the solutions can also be utilized to determine that a transport has been damaged by using sensor data to identify a new condition of the transport during a transport event and comparing the condition to a transport condition profile, making it possible to safely and securely capture critical data from a transport that is about to be engaged in a detrimental event.

In one embodiment, the solutions can also be utilized to warn occupants of a transport when the transport, via one or more sensors, has determined that it is approaching or going down a one-way road the incorrect way. The transport has sensors/cameras/maps interacting with the system of the current solution. The system knows the geographic location of one-way streets. The system may audibly inform the occupants, "Approaching a one-way street", for example. In one embodiment, the solutions can also be utilized to allow the transport to get paid allowing autonomous vehicle owners to monetize the data their vehicle sensors collect and store creating an incentive for vehicle owners to share their data and provide entities with additional data through which to improve the performance of future vehicles, provide services to the vehicle owners, etc.

In one embodiment, the solutions can also be utilized to either increase or decrease a vehicle's features according to the action of the vehicle over a period of time. In one embodiment, the solutions can also be utilized to assign a fractional ownership to a transport. Sensor data related to one or more transports and a device proximate to the transport are used to determine a condition of the transport. The fractional ownership of the transport is determined based on the condition and a new responsibility of the transport is provided. In one embodiment, the solutions can also be utilized to provide data to a replacement/upfitting component, wherein the data attempts to subvert an authorized functionality of the replacement/upfitting component, and responsive to a non-subversion of the authorized functionality, permitting, by the component, use of the authorized functionality of the replacement/upfitting component.

In one embodiment, the solutions can also be utilized to provide individuals the ability to ensure that an occupant should be in a transport and for that occupant to reach a particular destination. Further, the system ensures a driver (if a non-autonomous transport) and/or other occupants are authorized to interact with the occupant. Also, pickups, drop-offs and location are noted. All of the above are stored in an immutable fashion on a blockchain. In one embodiment, the solutions can also be utilized to determine characteristics of a driver via an analysis of driving style and other elements to take action in the event that the driver is not driving in a normal manner, such as a manner in which the driver has previously driven in a particular condition, for example during the day, at night, in the rain, in the snow, etc. Further, the attributes of the transport are also taken into account. Attributes consist of weather, whether the headlights are on, whether navigation is being used, a HUD is being used, volume of media being played, etc. In one embodiment, the solutions can also be utilized to notify occupants in a transport of a dangerous situation when items inside the transport signify that the occupants may not be aware of the dangerous situation.

In one embodiment, the solutions can also be utilized to mount calibration devices on a rig that is fixed to a vehicle wherein the various sensors on the transport are able to automatically self-adjust based on what should be detected by the calibration devices as compared to what is actually detected. In one embodiment, the solutions can also be utilized to use a blockchain to require consensus from a plurality of service centers when a transport needing service sends malfunction information allowing remote diagnostic functionality wherein a consensus is required from other service centers on what a severity threshold is for the data. Once the consensus is received, the service center may send the malfunction security level to the blockchain to be stored. In one embodiment, the solutions can also be utilized to determine a difference in sensor data external to the transport and the transport's own sensor data. The transport requests, from a server, a software to rectify the issue. In one embodiment, the solutions can also be utilized to allow for the messaging of transports that are either nearby, or in the area, when an event occurs (e.g. a collision).

Figure 2I:
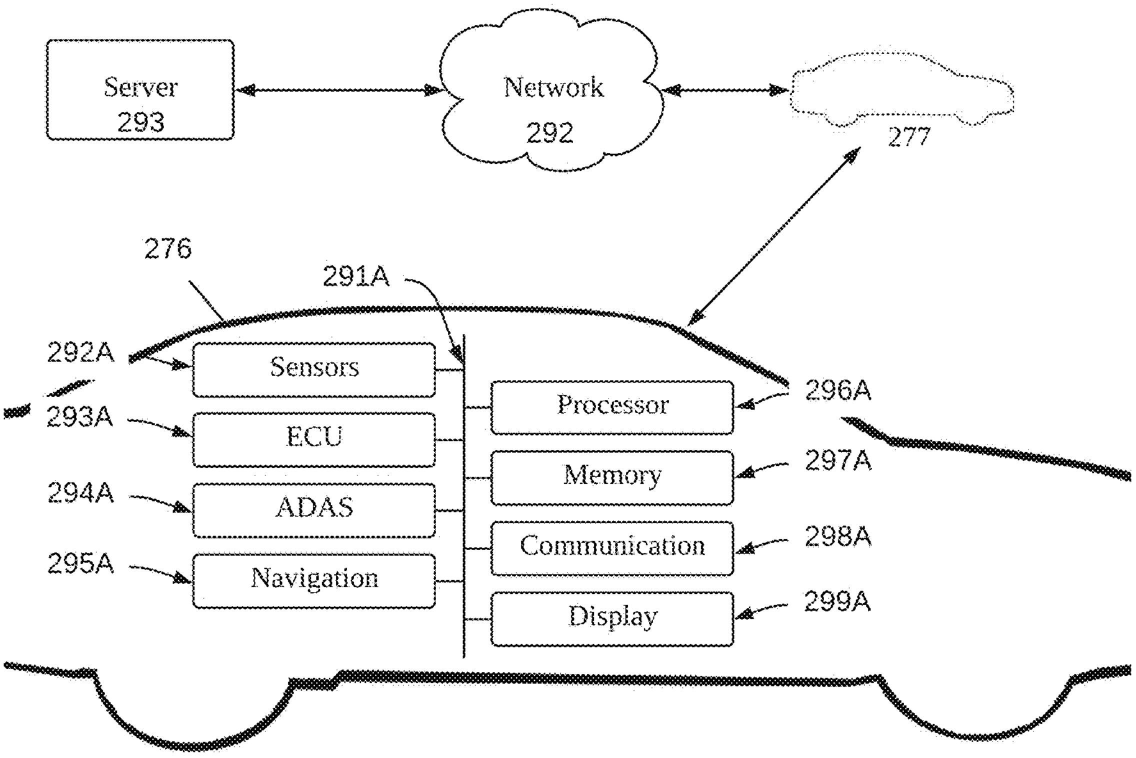
FIG. 2I illustrates yet a further diagram depicting interconnections between elements, according to example embodiments.

Referring to FIG. 2I, an operating environment 290A for a connected transport is illustrated according to some embodiments. As depicted, the transport 276 includes a Controller Area Network (CAN) bus 291A connecting elements 292A-299A of the transport. Other elements may be connected to the CAN bus and are not depicted herein. The depicted elements connected to the CAN bus include a sensor set 292A, Electronic Control Units 293A, autonomous features or Advanced Driver Assistance Systems (ADAS) 294A, and the navigation system 295A. In some embodiments, the transport 276 includes a processor 296A, a memory 297A, a communication unit 298A, and an electronic display 299A.

The processor 296A includes an arithmetic logic unit, a microprocessor, a general-purpose controller, and/or a similar processor array to perform computations and provide electronic display signals to a display unit 299A. The processor 296A processes data signals and may include various computing architectures including a complex instruction set computer (CISC) architecture, a reduced instruction set computer (RISC) architecture, or an architecture implementing a combination of instruction sets. The transport 276 may include one or more processors 296A. Other processors, operating systems, sensors, displays, and physical configurations that are communicably coupled to one another (not depicted) may be used with the instant solution.

Memory 297A is a non-transitory memory storing instructions or data that may be accessed and executed by the processor 296A. The instructions and/or data may include code to perform the techniques described herein. The memory 297A may be a dynamic random-access memory (DRAM) device, a static random-access memory (SRAM) device, flash memory, or some other memory device. In some embodiments, the memory 297A also may include non-volatile memory or a similar permanent storage device and media which may include a hard disk drive, a floppy disk drive, a CD-ROM device, a DVD-ROM device, a DVD-RAM device, a DVD-RW device, a flash memory device, or some other mass storage device for storing information on a permanent basis. A portion of the memory 297A may be reserved for use as a buffer or virtual random-access memory (virtual RAM). The transport 276 may include one or more memories 297A without deviating from the current solution.

The memory 297A of the transport 276 may store one or more of the following types of data: navigation route data 295A, and autonomous features data 294A. In some embodiments, the memory 297A stores data that may be necessary for the navigation application 295A to provide the functions.

The navigation system 295A may describe at least one navigation route including a start point and an endpoint. In some embodiments, the navigation system 295A of the transport 276 receives a request from a user for navigation routes wherein the request includes a starting point and an ending point. The navigation system 295A may query a real-time data server 293 (via a network 292), such as a server that provides driving directions, for navigation route data corresponding to navigation routes including the start point and the endpoint. The real-time data server 293 transmits the navigation route data to the transport 276 via a wireless network 292 and the communication system 298A stores the navigation data 295A in the memory 297A of the transport 276.

The ECU 293A controls the operation of many of the systems of the transport 276, including the ADAS systems 294A. The ECU 293A may, responsive to instructions received from the navigation system 295A, deactivate any unsafe and/or unselected autonomous features for the duration of a journey controlled by the ADAS systems 294A. In this way, the navigation system 295A may control whether ADAS systems 294A are activated or enabled so that they may be activated for a given navigation route.

The sensor set 292A may include any sensors in the transport 276 generating sensor data. For example, the sensor set 292A may include short-range sensors and long-range sensors. In some embodiments, the sensor set 292A of the transport 276 may include one or more of the following vehicle sensors: a camera, a LIDAR sensor, an ultrasonic sensor, an automobile engine sensor, a radar sensor, a laser altimeter, a manifold absolute pressure sensor, an infrared detector, a motion detector, a thermostat, a sound detector, a carbon monoxide sensor, a carbon dioxide sensor, an oxygen sensor, a mass airflow sensor, an engine coolant temperature sensor, a throttle position sensor, a crankshaft position sensor, a valve timer, an air-fuel ratio meter, a blind spot meter, a curb feeler, a defect detector, a Hall effect sensor, a parking sensor, a radar gun, a speedometer, a speed sensor, a tire-pressure monitoring sensor, a torque sensor, a transmission fluid temperature sensor, a turbine speed sensor (TSS), a variable reluctance sensor, a vehicle speed sensor (VSS), a water sensor, a wheel speed sensor, a GPS sensor, a mapping functionality, and any other type of automotive sensor. The navigation system 295A may store the sensor data in the memory 297A.

The communication unit 298A transmits and receives data to and from the network 292 or to another communication channel. In some embodiments, the communication unit 298A may include a DSRC transceiver, a DSRC receiver and other hardware or software necessary to make the transport 276 a DSRC-equipped device.

The transport 276 may interact with other transports 277 via V2V technology. V2V communication includes sensing radar information corresponding to relative distances to external objects, receiving GPS information of the transports, setting areas as areas where the other transports 277 are located based on the sensed radar information, calculating probabilities that the GPS information of the object vehicles will be located at the set areas, and identifying transports and/or objects corresponding to the radar information and the GPS information of the object vehicles based on the calculated probabilities, in one embodiment.

In one embodiment, the solutions described and depicted herein can be utilized to manage emergency scenarios and transport features when a transport is determined to be entering an area without network access. In one embodiment, the solutions can also be utilized to manage and provide features in a transport (such as audio, video, navigation, etc.) without network connection. In one embodiment, the solutions can also be utilized to determine when a profile of a person in proximity to the transport matches profile attributes of a profile of at least one occupant in the transport. A notification is sent from the transport to establish communication.

In one embodiment, the solutions can also be utilized to analyze the availability of occupants in respective transports that are available for a voice communication based on an amount of time remaining in the transport and context of the communication to be performed. In one embodiment, the solutions can also be utilized to determine two levels of threat of roadway obstruction and receiving a gesture that may indicate that the obstruction is not rising to an alert above a threshold, and proceeding, by the transport along the roadway. In one embodiment, the solutions can also be utilized to delete sensitive data from a transport when the transport has had damage such that it is rendered unable to be used.

In one embodiment, the solutions can also be utilized to verify that the customer data to be removed has truly been removed from all of the required locations within the enterprise demonstrating GDPR compliance. In one embodiment, the solutions can also be utilized to provide consideration from one transport to another transport in exchange for data related to safety, important notifications, etc. to enhance the autonomous capabilities of the lower level autonomous vehicle. In one embodiment, the solutions can also be utilized to provide an ability for a transport to receive data based on a first biometric associated with an occupant. Then the transport unencrypts the encrypted data based on a verification of a second biometric, wherein the second biometric is a continuum of the first biometric. The transport provides the unencrypted data to the occupant when only the occupant is able to receive the unencrypted data and deletes a sensitive portion of the unencrypted data as the sensitive portion is being provided and a non-sensitive portion after a period of time associated with the biometric elapses. In one embodiment, the solutions can also be utilized to provide an ability for a transport to validate an individual based on a weight and grip pressure applied to the steering wheel of the transport. In one embodiment, the solutions can also be utilized to provide a feature to a car that exists but is not currently enabled presenting features to an occupant of the automobile that reflects the occupant's characteristics.

In one embodiment, the solutions can also be utilized to allow for the modification of a transport, particularly the interior of the transport as well as the exterior of the transport to reflect, and assist at least one occupant, in one embodiment. In another embodiment, recreating an occupant's work and/or home environment is disclosed. The system may attempt to "recreate" the user's work/home environment while the user is in the transport if it determines that the user is in "work mode" or "home mode". All data related to the interior and exterior of the transport as well as the various occupants utilizing the transport are stored on a blockchain and executed via smart contracts. In one embodiment, the solutions can also be utilized to detect occupant gestures to assist in communicating with nearby transports wherein the transport may maneuver accordingly. In one embodiment, the solutions can also be utilized to provide the ability for a transport to detect intended gestures using a gesture definition datastore. In one embodiment, the solutions can also be utilized to provide an ability for a transport to take various actions based on a gait and a gesture of a user. In one embodiment, the solutions can also be utilized to ensure that a driver of a transport that is currently engaged in various operations (for example, driving while talking with navigation on, etc.) does not exceed an unsafe number of operations before being permitted to gesture.

In one embodiment, the solutions can also be utilized to assign a status to each occupant in a transport and validating a gesture from an occupant based on the occupant's status. In one embodiment, the solutions can also be utilized to collect details of sound related to a collision (in what location, in what direction, rising or falling, from what device, data associated with the device such as type, manufacturer, owner, as well as the number of contemporaneous sounds, and the times the sounds were emanated, etc.) and provide to the system where analysis of the data assists in determining details regarding the collision. In one embodiment, the solutions can also be utilized to provide a determination that a transport is unsafe to operate. The transport includes multiple components that interoperate to control the transport, and each component is associated with a separate component key. A cryptographic key is sent to the transport to decrease transport functionality. In response to receiving the cryptographic key, the transport disables one or more of the component keys. Disabling the one or more component keys results in one or more of limiting the transport to not move greater than a given speed, limiting the transport to not come closer than a distance to another transport, and limiting the transport to not travel greater than a threshold distance.

In one embodiment, the solutions can also be utilized to provide an indication from one specific transport (that is about to vacate a location) to another specific transport (that is seeking to occupy a location), a blockchain is used to perform authentication and coordination. In one embodiment, the solutions can also be utilized to determine a fractional responsibility for a transport. Such as the case where multiple people own a single transport, and the use of the transport, which may change over a period of time, is used by the system to update the fractional ownership. Other embodiments will be included in the application including a minimal ownership of a transport based on not the use of the transport, but the availability of the transport, and the determination of the driver of the transport as well as others.

In one embodiment, the solutions can also be utilized to permit in a transport a user to his/her subscriptions with a closed group of people such as family members or friends. For example, a user might want to share a membership, and if so, associated transactions are stored in a blockchain or traditional database. When the subscribed materials are requested by a user, who is not a primary subscriber, a blockchain node (i.e., a transport) can verify that a person requesting a service is an authorized person with whom the subscriber has shared the profile. In one embodiment, the solutions can also be utilized to allow a person to utilize supplemental transport(s) to arrive at an intended destination. A functional relationship value (e.g. value that indicates the various parameters and their importance in determining what type of alternate transport to utilize) is used in determining the supplemental transport. In one embodiment, the solutions can also be utilized to allow the occupants in an accident to have access to other transports to continue to their initial destination.

In one embodiment, the solutions can also be utilized to propagate a software/firmware upload to a first subset of transports. This first set of transports test the update, and when the test is successful, the update is propagated to a further set of transports. In one embodiment, the solutions can also be utilized to propagate software/firmware updates to vehicles from a master transport where the update is propagated through the network of vehicles from a first subset, then a larger subset, etc. A portion of the update may be first sent, then the remaining portion sent from the same or another vehicle. In one embodiment, the solutions can also be utilized to provide an update for a transport's computer to the transport and a transport operator's/occupant's device. The update is maybe authorized by all drivers and/or all occupants. The software update is provided to the vehicle and the device(s). The user does not have to do anything but go proximate to the vehicle and the functionality automatically occurs. A notification is sent to the device(s) indicating that the software update is completed. In one embodiment, the solutions can also be utilized to validate that an OTA software update is performed by a qualified technician and generation, by the one or more transport components, of a status related to: an originator of the validation code, a procedure for wirelessly receiving the software update, information contained in the software update, and results of the validation.

In one embodiment, the solutions can also be utilized to provide the ability to parse a software update located in a first component by a second component. Then verifying the first portion of critical updates and a second portion of non-critical updates, assigning the verified first portion to one process in the transport, running the verified first portion with the one process for a period of time, and responsive to positive results based on the period of time, running the verified first portion with other processes after the period of time. In one embodiment, the solutions can also be utilized to provide a selection of services to an occupant where the services are based on a profile of an occupant of the transport, and a shared profile which is shared with the profile of the occupant. In one embodiment, the solutions can also be utilized to store user profile data in a blockchain and intelligently present offers and recommendations to a user based on the user's automatically gathered history of purchases and preferences acquired from the user profile on the blockchain.

For a transport to be adequately secured, the transport must be protected from unauthorized physical access as well as unauthorized remote access (e.g., cyber-threats). To prevent unauthorized physical access, a transport is equipped with a secure access system such as a keyless entry in one embodiment. Meanwhile, security protocols are added to a transport's computers and computer networks to facilitate secure remote communications to and from the transport in one embodiment.

Electronic Control Units (ECUs) are nodes within a transport that control tasks such as activating the windshield wipers to tasks such as an anti-lock brake system. ECUs are often connected to one another through the transport's central network, which may be referred to as a controller area network (CAN). State of the art features such as autonomous driving are strongly reliant on the implementation of new, complex ECUs such as advanced driver-assistance systems (ADAS), sensors, and the like. While these new technologies have helped improve the safety and driving experience of a transport, they have also increased the number of externally-communicating units inside of the transport making them more vulnerable to attack. Below are some examples of protecting the transport from physical intrusion and remote intrusion.

Figure 2J:
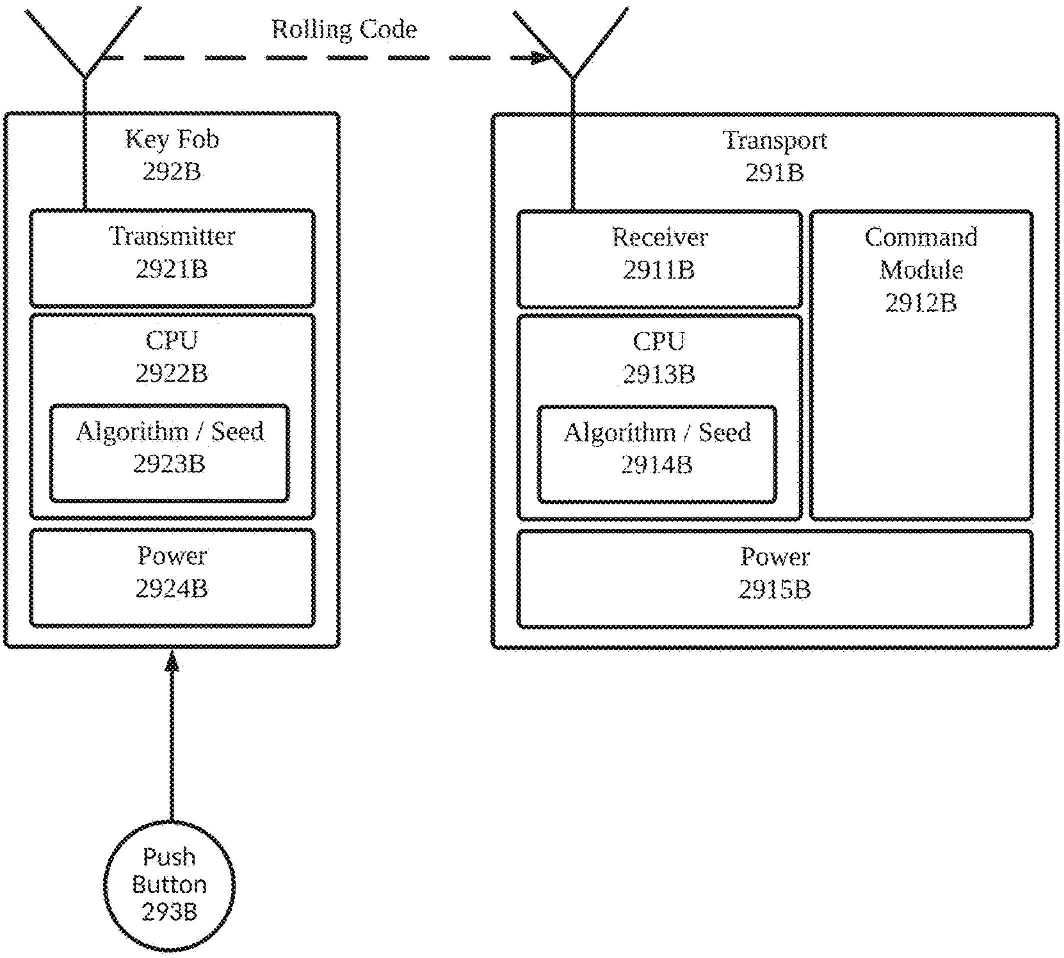
FIG. 2J illustrates yet a further diagram depicting a keyless entry system, according to example embodiments.

FIG. 2J illustrates a keyless entry system 290B to prevent unauthorized physical access to a transport 291B, according to example embodiments. Referring to FIG. 2J, a key fob 292B transmits commands to a transport 291B using radio frequency signals in one embodiment. In this example, the key fob 292B includes a transmitter 2921B with an antenna that is capable of sending short-range wireless radio signals. The transport 291B includes a receiver 2911B with an antenna that is capable of receiving the short-range wireless signal transmitted from the transmitter 2921B. The key fob 292B and the transport 291B also include CPUs 2922B and 2913B, respectively, which control the respective devices. Here, a memory of the CPUs 2922B and 2913B (or accessible to the CPUs). Each of the key fob 292B and the transport 291B includes power supplies 2924B and 2915B for powering the respective devices in one embodiment.

When the user presses a button 293B (or otherwise actuates the fob, etc.) on the key fob 292B, the CPU 2922B wakes up inside the key fob 292B and sends a data stream to the transmitter 2921B which is output via the antenna. In other embodiments, the user's intent is acknowledged on the key fob 292B via other means, such as via a microphone that accepts audio, a camera that captures images and/or video, or other sensors that are commonly utilized in the art to detect intent from a user including receiving gestures, motion, eye movements, and the like. The data stream may be a 64 bit to 128 bit long signal which includes one or more of a preamble, a command code, and a rolling code. The signal may be sent at a rate between 2 KHz and 20 KHz, but embodiments are not limited thereto. In response, the receiver 2911B of the transport 291B captures the signal from the transmitter 2921B, demodulates the signal, and sends the data stream to the CPU 2913B which decodes the signal and sends commands (e.g., lock the door, unlock the door, etc.) to a command module 2912B.

If the key fob 292B and the transport 291B use a fixed code between them, replay attacks can be performed. In this case, if the attacker is able to capture/sniff the fixed code during the short-range communication, the attacker could replay this code to gain entry into the transport 291B. To improve security, the key fob and the transport 291B may use a rolling code that changes after each use. Here, the key fob 292B and the transport 291B are synchronized with an initial seed 2923B (e.g., a random number, pseudo random number, etc.) This is referred to as pairing. The key fob 292B and the transport 291B also include a shared algorithm for modifying the initial seed 2914B each time the button 293B is pressed. The following keypress will take the result of the previous keypress as an input and transform it into the next number in the sequence. In some cases, the transport 291B may store multiple next codes (e.g., 255 next codes) in case the keypress on the key fob 292B is not detected by the transport 291B. Thus, a number of keypress on the key fob 292B that are unheard by the transport 291B do not prevent the transport from becoming out of sync.

In addition to rolling codes, the key fob 292B and the transport 291B may employ other methods to make attacks even more difficult. For example, different frequencies may be used for transmitting the rolling codes. As another example, two-way communication between the transmitter 2921B and the receiver 2911B may be used to establish a secure session. As another example, codes may have limited expirations or timeouts. Further, the instant solution as described and depicted with respect to FIG. 2J can be utilized in this and other networks and/or systems including those that are described and depicted herein.

Figure 2K:
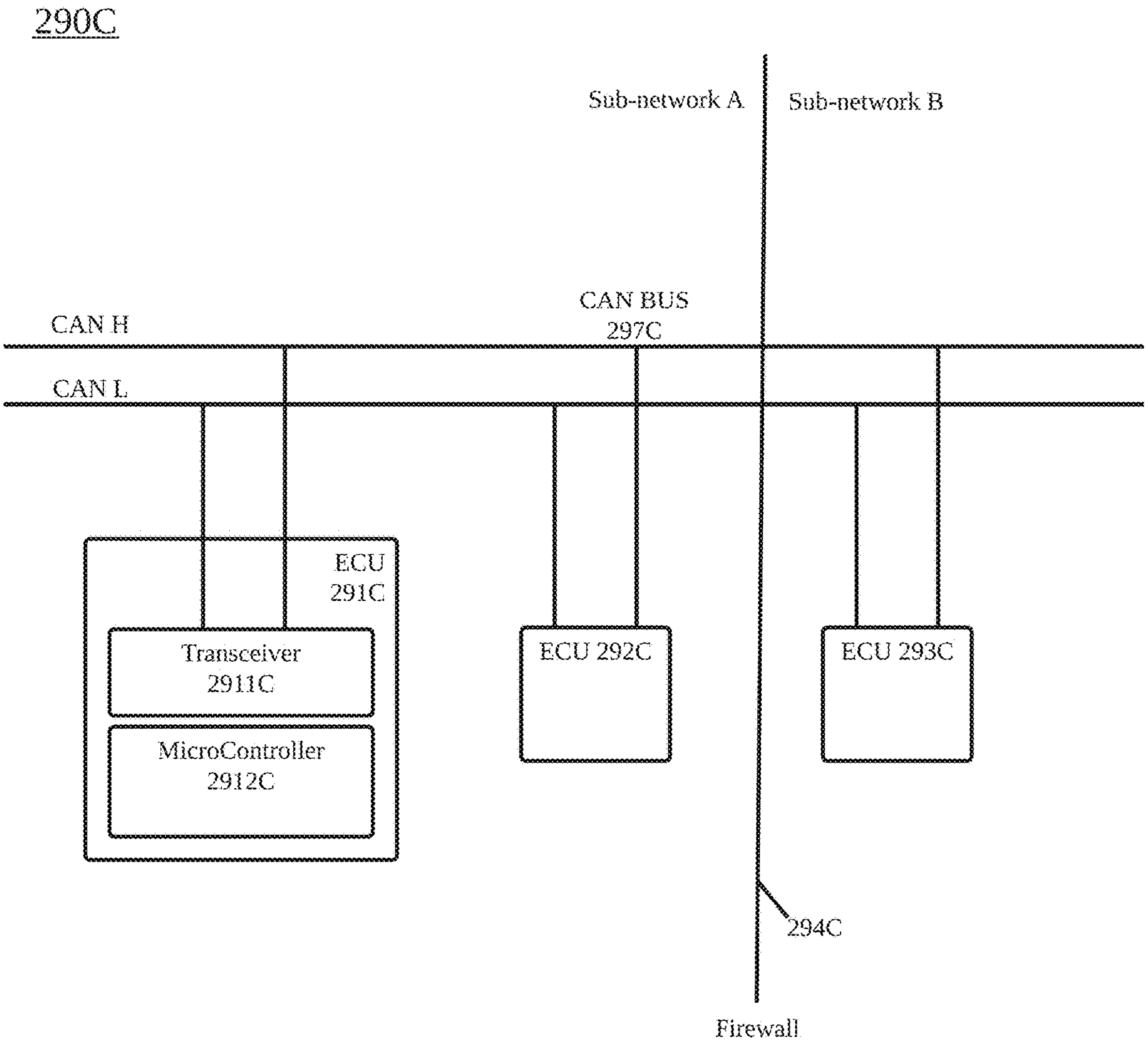
FIG. 2K illustrates yet a further diagram depicting a CAN within a transport, according to example embodiments.

FIG. 2K illustrates a controller area network (CAN) 290C within a transport, according to example embodiments. Referring to FIG. 2K, the CAN 290C includes a CAN bus 297C with a high and low terminal, and plurality of electronic control units (ECUs) 291C, 292C, 293C, etc. which are connected to the CAN bus 297C via wired connections. The CAN bus 297C is designed to allow microcontrollers and devices to communicate with each other in an application without a host computer. The CAN bus 297C implements a message-based protocol (i.e., ISO 11898 standards) that allows ECUs 291C-293C to send commands to one another at a root level. Meanwhile, the ECUs 291C-293C represent controllers for controlling electrical systems or subsystems within the transport. Examples of the electrical systems include power steering, anti-lock brakes, air-conditioning, tire pressure monitoring, cruise control, and many other features.

In this example, the ECU 291C includes a transceiver 2911C and a microcontroller 2912C. The transceiver may be used to transmit and receive messages to and from the CAN bus 297C. For example, the transceiver 2911C may convert the data from the microcontroller 2912C into a format of the CAN bus 297C and also convert data from the CAN bus 297C into a format for the microcontroller 2912C. Meanwhile, the microcontroller 2912C interprets the messages and also decide what messages to send using ECU software installed therein in one embodiment.

In order to protect the CAN 290C from cyber-threats, various security protocols may be implemented. For example, sub-networks (e.g., sub-networks A and B, etc.) may be used to divide the CAN 290C into smaller sub-CANs and limit an attacker's capabilities to access the transport remotely. In the example of FIG. 2K, ECUs 291C and 292C may be part of a same sub-network while ECU 293C is part of an independent sub-network. Furthermore, a firewall 294C (or gateway, etc.) may be added to block messages from crossing the CAN bus 297C across sub-networks. If an attacker gains access to one sub-network, the attacker will not have access to the entire network. To make sub-networks even more secure, the most critical ECUs are not placed on the same sub-network, in one embodiment.

Although not shown in FIG. 2K, other examples of security controls within a CAN include an intrusion detection system (IDS) which can be added to each sub-network and read all data passing to detect malicious messages. If a malicious message is detected, the IDS can notify the automobile user. Other possible security protocols include encryption/security keys that can be used to obscure messages. As another example, authentication protocols are implemented that enable a message to authenticate itself, in one embodiment.

In addition to protecting a transport's internal network, transports may also be protected when communicating with external networks such as the Internet. One of the benefits of having a transport connected to a data source such as the Internet is that information from the transport can be sent through a network to remote locations for analysis. Examples of transport information include GPS, onboard diagnostics, tire pressure, and the like. These communication systems are often referred to as telematics because they involve the combination of telecommunications and informatics. Further, the instant solution as described and depicted with respect to FIG. 2K can be utilized in this and other networks and/or systems including those that are described and depicted herein.

Figure 2L:
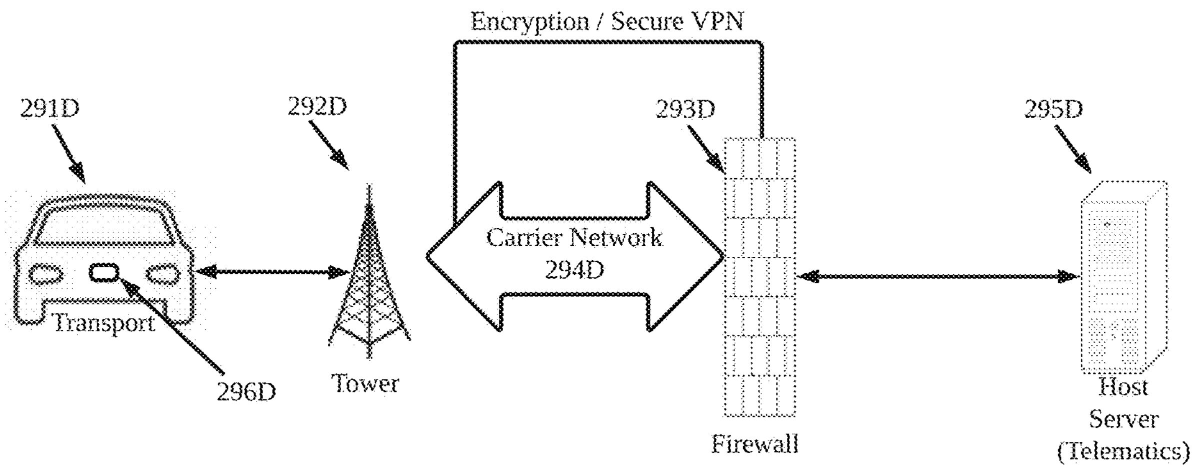
FIG. 2L illustrates yet a further diagram depicting an end-to-end communication channel, according to example embodiments.

FIG. 2L illustrates a secure end-to-end transport communication channel according to example embodiments. Referring to FIG. 2L, a telematics network 290D includes a transport 291D and a host server 295D that is disposed at a remote location (e.g., a web server, a cloud platform, a database, etc.) and connected to the transport 291D via a network such as the Internet. In this example, a device 296D associated with the host server 295D may be installed within the network inside the transport 291D. Furthermore, although not shown, the device 296D may connect to other elements of the transport 291D such as the CAN bus, an onboard diagnostics (ODBII) port, a GPS system, a SIM card, a modem, and the like. The device 296D may collect data from any of these systems and transfer the data to the server 295D via the network.

Secure management of data begins with the transport 291D. In some embodiments, the device 296D may collect information before, during, and after a trip. The data may include GPS data, travel data, passenger information, diagnostic data, fuel data, speed data, and the like. However, the device 296D may only communicate the collected information back to the host server 295D in response to transport ignition and trip completion. Furthermore, communication may only be initiated by the device 296D, and not by the host server 295D. As such, the device 296D will not accept communications initiated by outside sources in one embodiment.

To perform the communication, the device 296D may establish a secured private network between the device 296D and the host server 295D. Here, the device 296D may include a tamper-proof SIM card which provides secure access to a carrier network 294D, via a radio tower 292D. When preparing to transmit data to the host server 295D, the device 296D may establish a one-way secure connection with the host server 295D. The carrier network 294D may communicate with the host server 295D using one or more security protocols. As a non-limiting example, the carrier network 294D may communicate with the host server 295D via a VPN tunnel which allows access through a firewall 293D of the host server 295D. As another example, the carrier network 294D may use data encryption (e.g., AES encryption, etc.) when transmitting data to the host server 295D. In some cases, the system may use multiple security measures such as both a VPN and encryption to further secure the data.

In addition to communicating with external servers, transports may also communicate with each other. In particular, transport-to-transport (V2V) communication systems enable transports to communicate with each other, roadside infrastructures (e.g., traffic lights, signs, cameras, parking meters, etc.), and the like, over a wireless network. The wireless network may include one or more of a Wi-Fi networks, cellular networks, dedicated short range communication (DSRC) networks, and the like. Transports may use V2V communication to provide other transports with information about a transport's speed, acceleration, braking, and direction, to name a few. Accordingly, transports can receive insight of the conditions ahead before such conditions become visible thus greatly reducing collisions. Further, the instant solution as described and depicted with respect to FIG. 2L can be utilized in this and other networks and/or systems including those that are described and depicted herein.

Figure 2M:
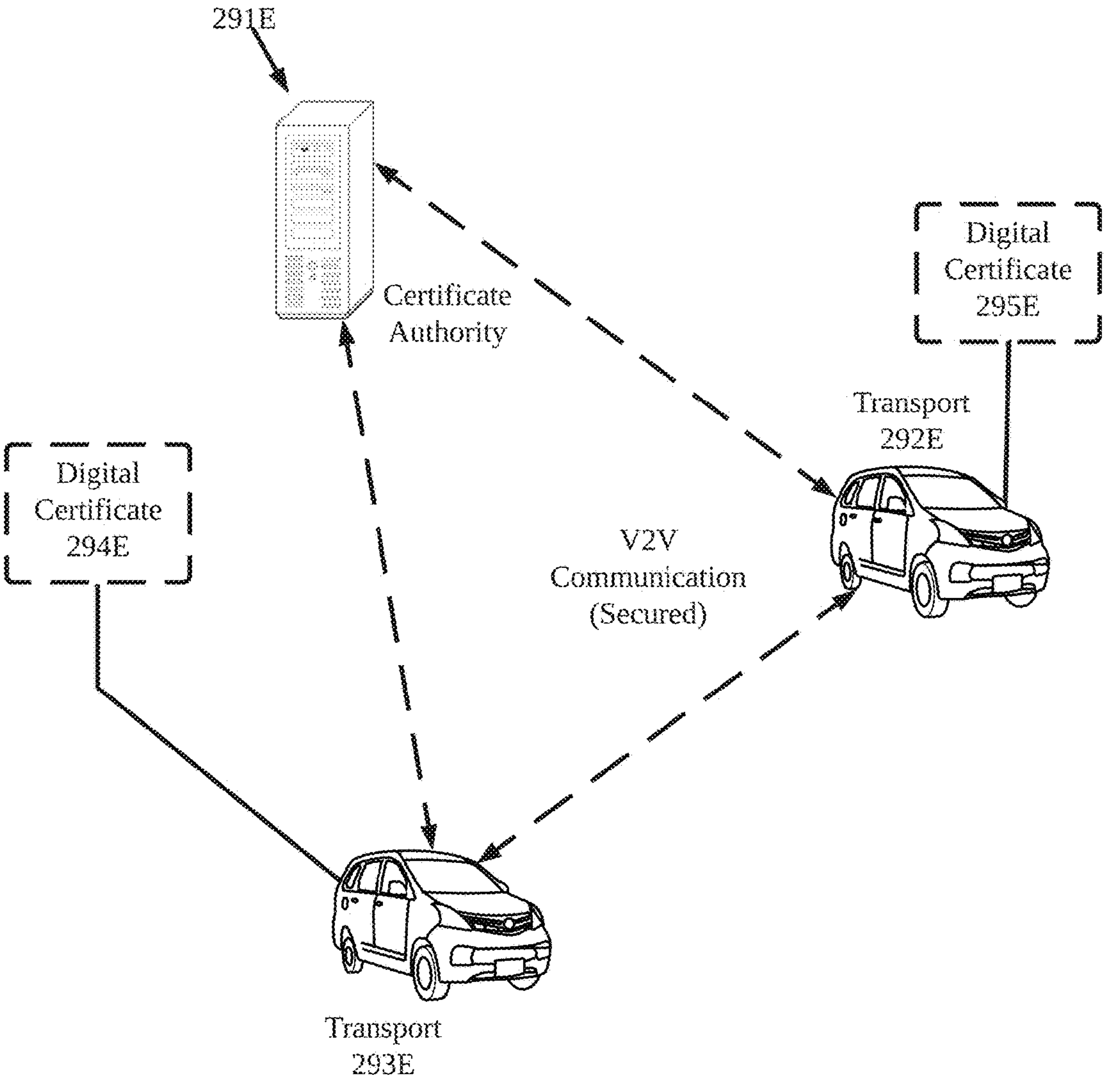
FIG. 2M illustrates yet a further diagram depicting an example of transports performing secured V2V communications using security certificates, according to example embodiments.

FIG. 2M illustrates an example 290E of transports 293E and 292E performing secured V2V communications using security certificates, according to example embodiments. Referring to FIG. 2M, the transports 293E and 292E may communicate with each other through V2V communications over a short-range network, a cellular network, or the like. Before sending messages, the transports 293E and 292E may sign the messages using a respective public key certificate. For example, the transport 293E may sign a V2V message using a public key certificate 294E. Likewise, the transport 292E may sign a V2V message using a public key certificate 295E. The public key certificates 294E and 295E are associated with the transports 293E and 292E, respectively in one embodiment.

Upon receiving the communications from each other, the transports may verify the signatures with a certificate authority 291E, or the like. For example, the transport 292E may verify with the certificate authority 291E that the public key certificate 294E used by transport 293E to sign a V2V communication is authentic. If the transport 292E successfully verifies the public key certificate 294E, the transport knows that the data is from a legitimate source. Likewise, the transport 293E may verify with the certificate authority 291E that the public key certificate 295E used by the transport 292E to sign a V2V communication is authentic. Further, the instant solution as described and depicted with respect to FIG. 2M can be utilized in this and other networks and/or systems including those that are described and depicted herein.

Figure 2N:
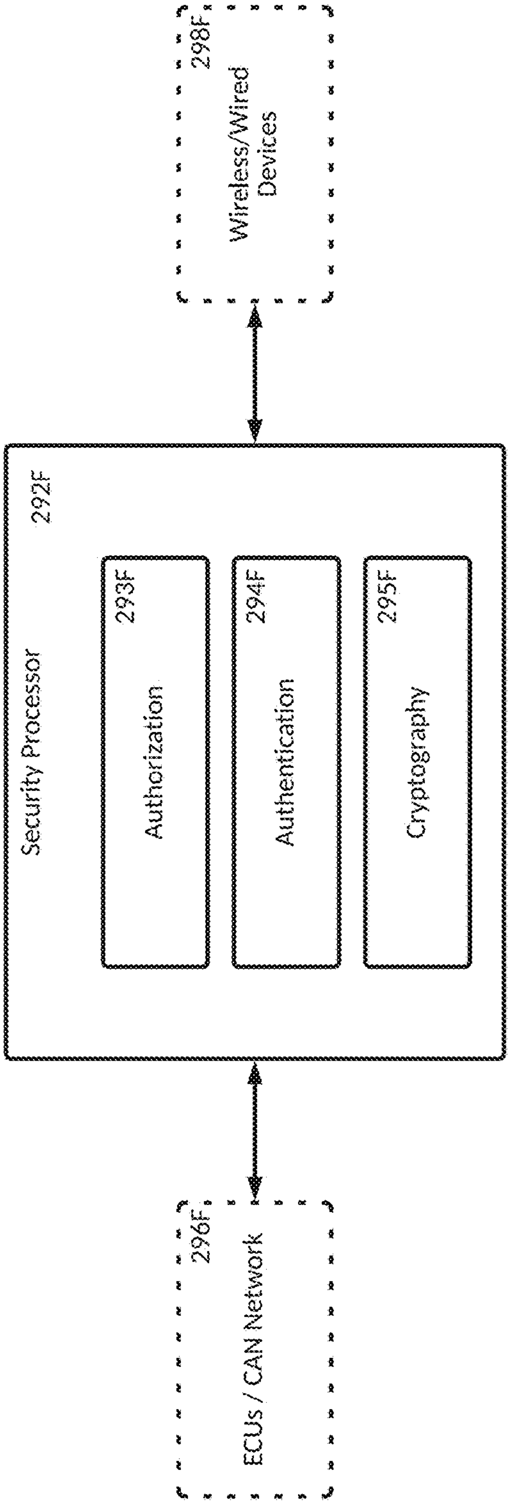
FIG. 2N illustrates yet a further diagram depicting an example of a transport interacting with a security processor and a wireless device, according to example embodiments.

FIG. 2N illustrates yet a further diagram 290F depicting an example of a transport interacting with a security processor and a wireless device, according to example embodiments. In some embodiments, the computer 224 shown in FIG. 2B may include security processor 292F as shown in the process 290F of the example of FIG. 2N. In particular, the security processor 292F may perform authorization, authentication, cryptography (e.g., encryption), and the like, for data transmissions that are sent between ECUs and other devices on a CAN bus of a vehicle, and also data messages that are transmitted between different vehicles.

In the example of FIG. 2N, the security processor 292F may include an authorization module 293F, an authentication module 294F, and a cryptography module 295F. The security processor 292F may be implemented within the transport's computer and may communicate with other elements of the transport, for example, the ECUs/CAN network 296F, wired and wireless devices 298F such as wireless network interfaces, input ports, and the like. The security processor 292F may ensure that data frames (e.g., CAN frames, etc.) that are transmitted internally within a transport (e.g., via the ECUs/CAN network 296F) are secure. Likewise, the security processor 292F can ensure that messages transmitted between different transports and to devices that are attached or connected via a wire to the transport's computer are also secured.

For example, the authorization module 293F may store passwords, usernames, PIN codes, biometric scans, and the like, for different users of the transport. The authorization module 293F may determine whether a user (or technician) has permission to access certain settings such as a transport's computer. In some embodiments, the authorization module may communicate with a network interface to download any necessary authorization information from an external server. When a user desires to make changes to the transport settings or modify technical details of the transport via a console or GUI within the transport, or via an attached/connected device, the authorization module 293F may require the user to verify themselves in some way before such settings are changed. For example, the authorization module 293F may require a username, a password, a PIN code, a biometric scan, a predefined line drawing or gesture, and the like. In response, the authorization module 293F may determine whether the user has the necessary permissions (access, etc.) being requested.

The authentication module 294F may be used to authenticate internal communications between ECUs on the CAN network of the vehicle. As an example, the authentication module 294F may provide information for authenticating communications between the ECUS. As an example, the authentication module 294F may transmit a bit signature algorithm to the ECUs of the CAN network. The ECUs may use the bit signature algorithm to insert authentication bits into the CAN fields of the CAN frame. All ECUs on the CAN network typically receive each CAN frame. The bit signature algorithm may dynamically change the position, amount, etc., of authentication bits each time a new CAN frame is generated by one of the ECUs. The authentication module 294F may also provide a list of ECUs that are exempt (safe list) and that do not need to use the authentication bits. The authentication module 294F may communicate with a remote server to retrieve updates to the bit signature algorithm, and the like.

The encryption module 295F may store asymmetric key pairs to be used by the transport to communicate with other external user devices and transports. For example, the encryption module 295F may provide a private key to be used by the transport to encrypt/decrypt communications while the corresponding public key may be provided to other user devices and transports to enable the other devices to decrypt/encrypt the communications. The encryption module 295F may communicate with a remote server to receive new keys, updates to keys, keys of new transports, users, etc., and the like. The encryption module 295F may also transmit any updates to a local private/public key pair to the remote server.

Figure 3A:
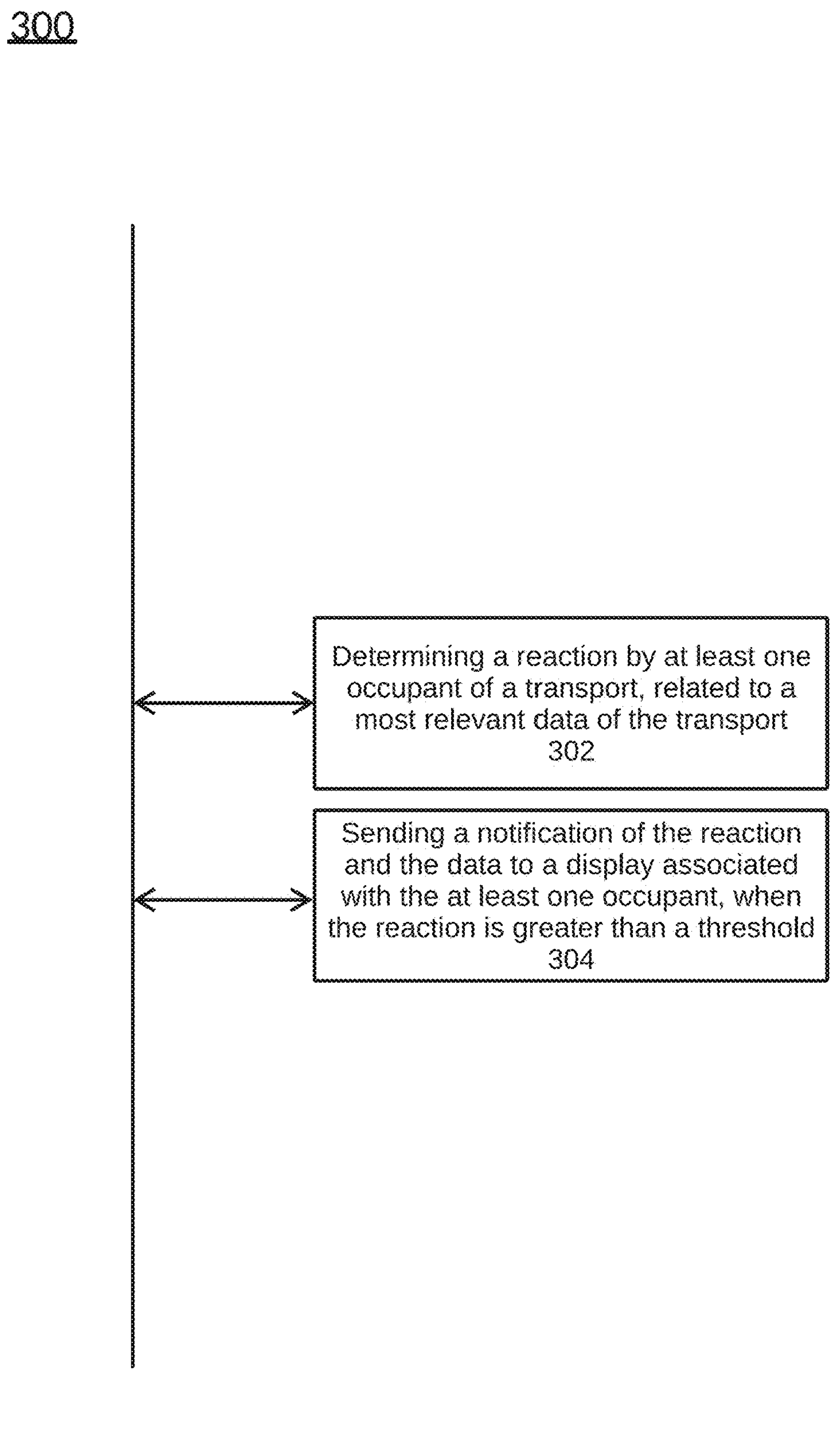
FIG. 3A illustrates a flow diagram, according to example embodiments.

FIG. 3A illustrates a flow diagram 300, according to example embodiments. Referring to FIG. 3A, the solution includes one or more of determining a reaction by at least one occupant of a transport, related to a most relevant data of the transport 302, and sending a notification of the reaction and the data to a display associated with the at least one occupant, when the reaction is greater than a threshold 304.

Figure 3B:
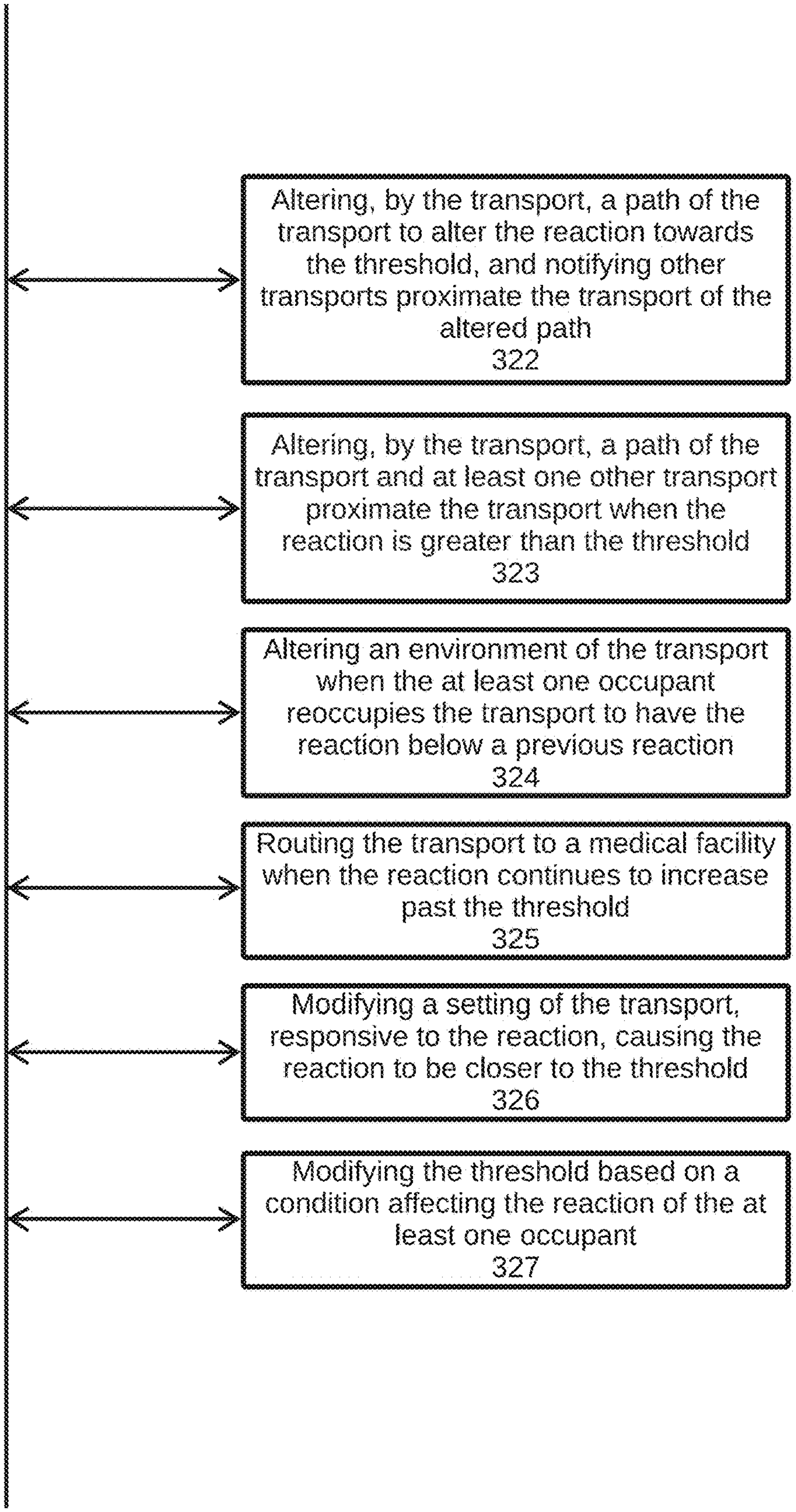
FIG. 3B illustrates another flow diagram, according to example embodiments.

FIG. 3B illustrates another flow diagram 320, according to example embodiments. Referring to FIG. 3B, the solution includes one or more of altering, by the transport, a path of the transport to alter the reaction towards the threshold, and notifying other transports proximate the transport of the altered path 322, altering, by the transport, a path of the transport and at least one other transport proximate the transport when the reaction is greater than the threshold 323, altering an environment of the transport when the at least one occupant reoccupies the transport to have the reaction below a previous reaction 324, routing the transport to a medical facility when the reaction continues to increase past the threshold 325, modifying a setting of the transport, responsive to the reaction, causing the reaction to be closer to the threshold 326, and modifying the threshold based on a condition affecting the reaction of the at least one occupant 327.

Figure 3C:
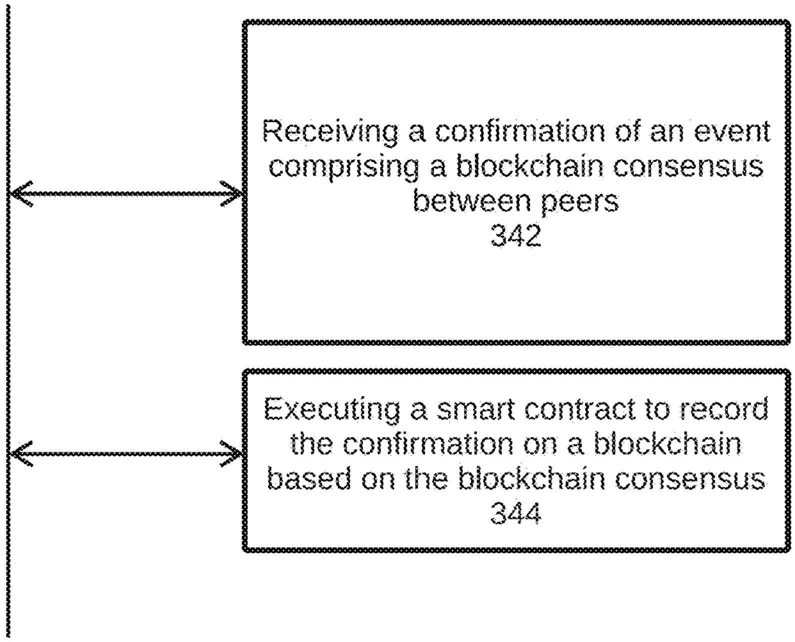
FIG. 3C illustrates yet another flow diagram, according to example embodiments.

FIG. 3C illustrates yet another flow diagram 340, according to example embodiments. Referring to FIG. 3C, the flow diagram includes one or more of receiving a confirmation of an event from one or more elements described or depicted herein, wherein the confirmation comprises a blockchain consensus between peers represented by any of the elements 342, and executing a smart contract to record the confirmation on a blockchain based on the blockchain consensus 344.

Figure 4:
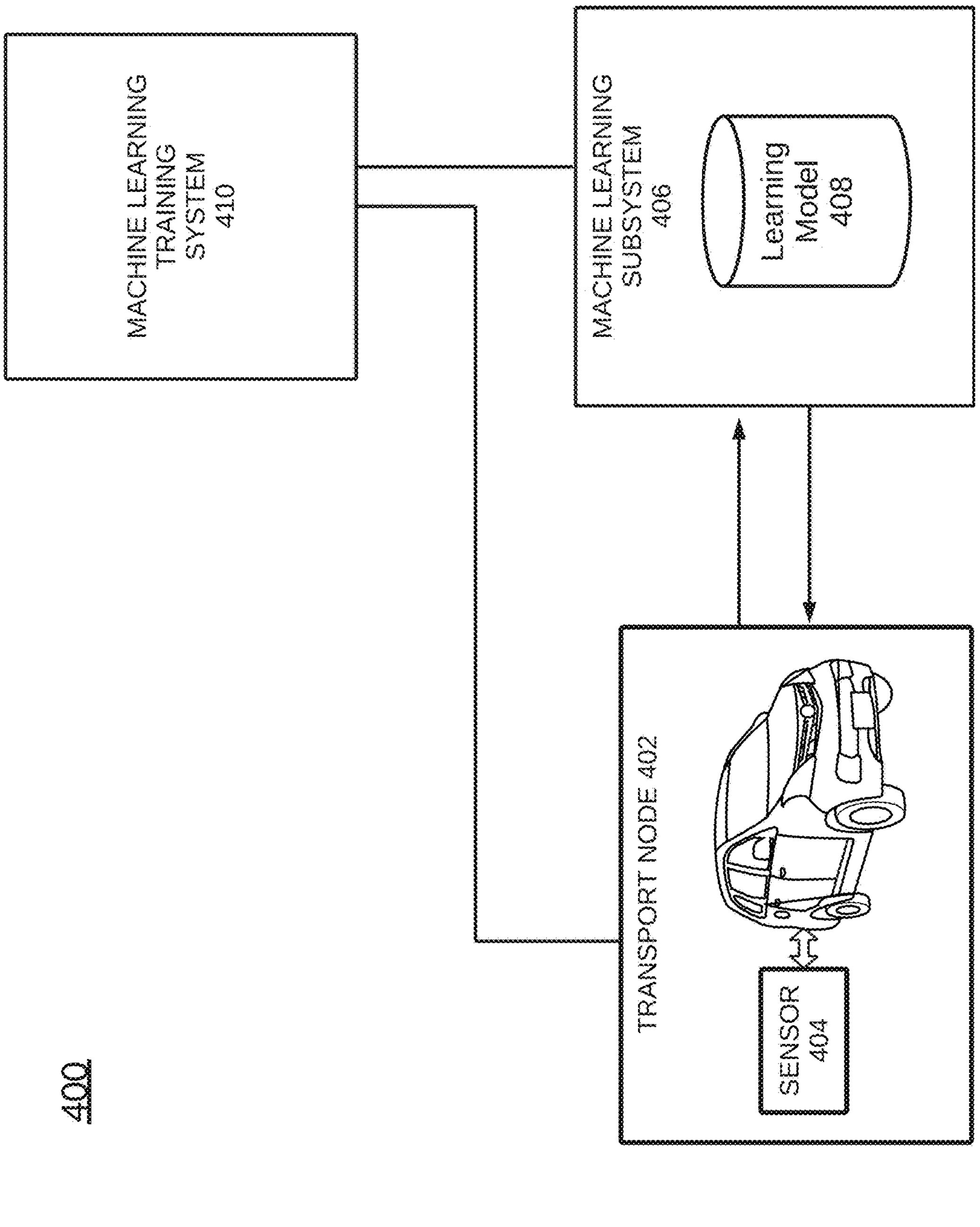
FIG. 4 illustrates a machine learning transport network diagram, according to example embodiments.

FIG. 4 illustrates a machine learning transport network diagram 400, according to example embodiments. The network 400 includes a transport 402 that interfaces with a machine learning subsystem 406. The transport includes one or more sensors 404.

The machine learning subsystem 406 contains a learning model 408, which is a mathematical artifact created by a machine learning training system 410 that generates predictions by finding patterns in one or more training data sets. In some embodiments, the machine learning subsystem 406 resides in the transport 402. In other embodiments, the machine learning subsystem 406 resides outside of the transport 402.

The transport 402 sends data from the one or more sensors 404 to the machine learning subsystem 406. The machine learning subsystem 406 provides the one or more sensor 404 data to the learning model 408, which returns one or more predictions. The machine learning subsystem 406 sends one or more instructions to the transport 402 based on the predictions from the learning model 408.

In a further embodiment, the transport 402 may send the one or more sensor 404 data to the machine learning training system 410. In yet another embodiment, the machine learning subsystem 406 may sent the sensor 404 data to the machine learning subsystem 410. One or more of the applications, features, steps, solutions, etc., described and/or depicted herein may utilize the machine learning network 400 as described herein.

Figure 5A:
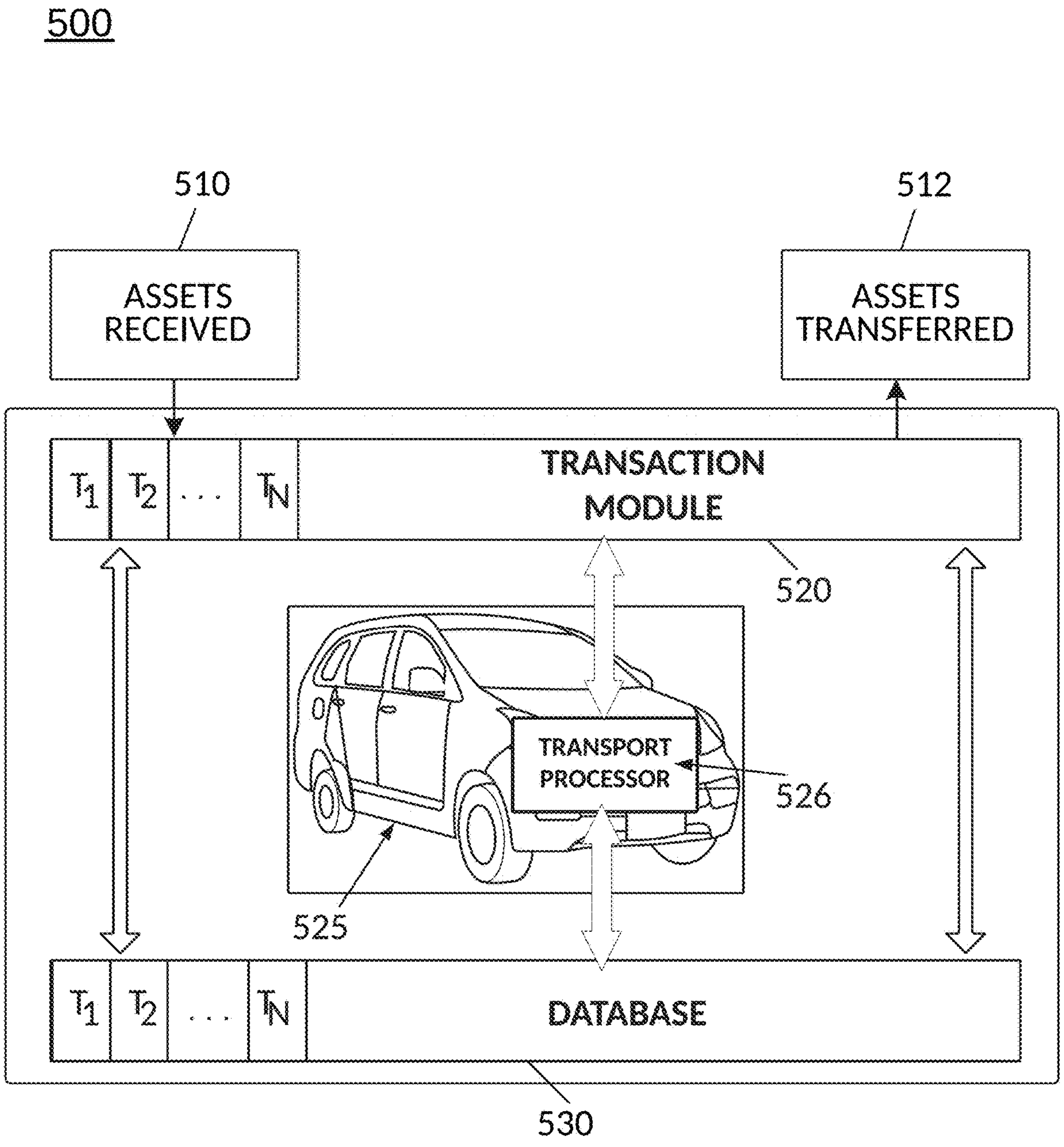
FIG. 5A illustrates an example vehicle configuration for managing database transactions associated with a vehicle, according to example embodiments.

FIG. 5A illustrates an example vehicle configuration 500 for managing database transactions associated with a vehicle, according to example embodiments. Referring to FIG. 5A, as a particular transport/vehicle 525 is engaged in transactions (e.g., vehicle service, dealer transactions, delivery/pickup, transportation services, etc.), the vehicle may receive assets 510 and/or expel/transfer assets 512 according to a transaction(s). A transport processor 526 resides in the vehicle 525 and communication exists between the transport processor 526, a database 530, a transport processor 526 and the transaction module 520. The transaction module 520 may record information, such as assets, parties, credits, service descriptions, date, time, location, results, notifications, unexpected events, etc. Those transactions in the transaction module 520 may be replicated into a database 530. The database 530 can be one of a SQL database, an RDBMS, a relational database, a non-relational database, a blockchain, a distributed ledger, and may be on board the transport, may be off board the transport, may be accessible directly and/or through a network, or be accessible to the transport.

Figure 5B:
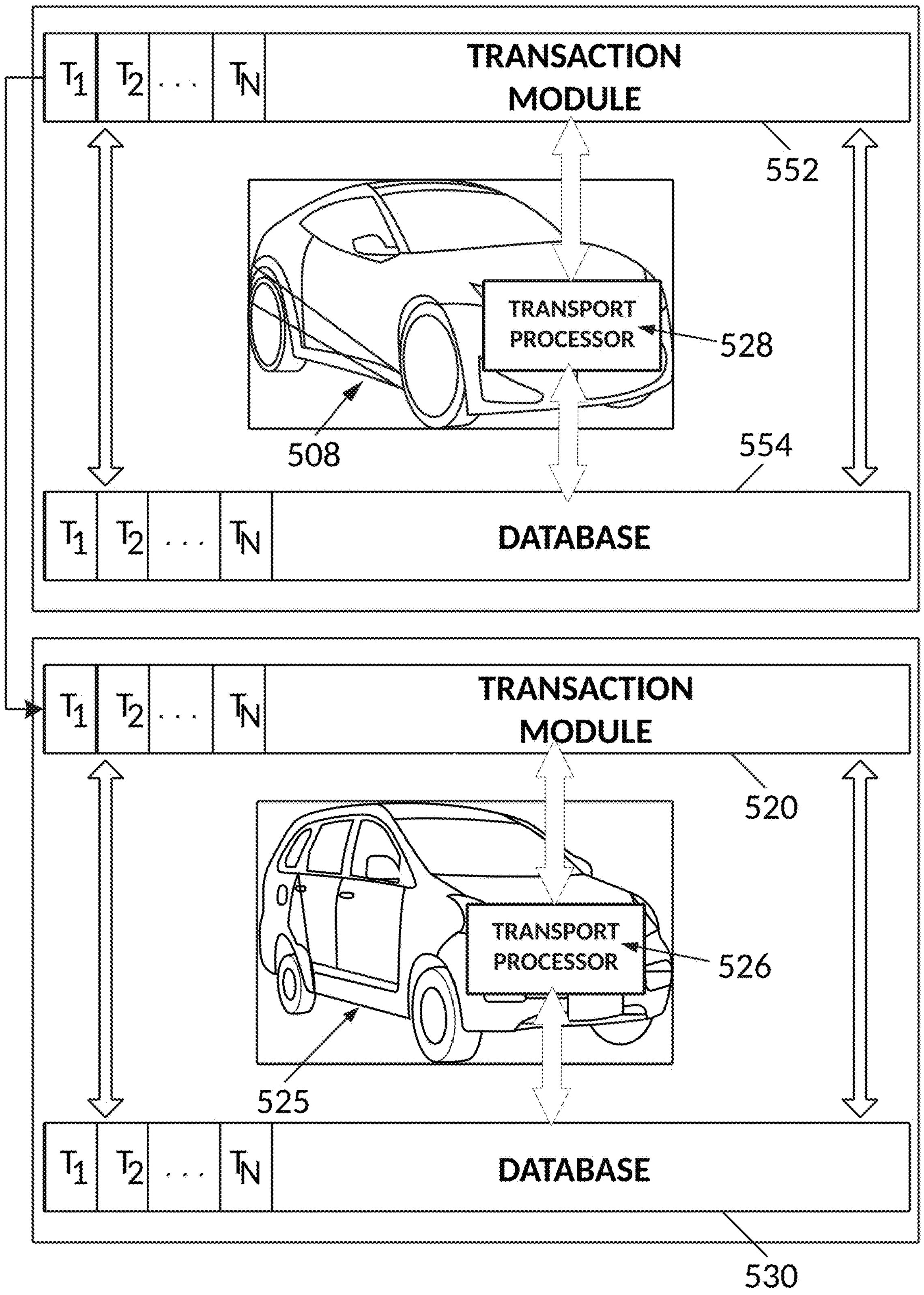
FIG. 5B illustrates another example vehicle configuration for managing database transactions conducted among various vehicles, according to example embodiments.

FIG. 5B illustrates an example vehicle configuration 550 for managing database transactions conducted among various vehicles, according to example embodiments. The vehicle 525 may engage with another vehicle 508 to perform various actions such as to share, transfer, acquire service calls, etc. when the vehicle has reached a status where the services need to be shared with another vehicle. For example, the vehicle 508 may be due for a battery charge and/or may have an issue with a tire and may be in route to pick up a package for delivery. A transport processor 528 resides in the vehicle 508 and communication exists between the transport processor 528, a database 554, and the transaction module 552. The vehicle 508 may notify another vehicle 525, which is in its network and which operates on its blockchain member service. A transport processor 526 resides in the vehicle 525 and communication exists between the transport processor 526, a database 530, the transport processor 526 and a transaction module 520. The vehicle 525 may then receive the information via a wireless communication request to perform the package pickup from the vehicle 508 and/or from a server (not shown). The transactions are logged in the transaction modules 552 and 520 of both vehicles. The credits are transferred from vehicle 508 to vehicle 525 and the record of the transferred service is logged in the database 530/554 assuming that the blockchains are different from one another, or are logged in the same blockchain used by all members. The database 554 can be one of a SQL database, an RDBMS, a relational database, a non-relational database, a blockchain, a distributed ledger, and may be on board the transport, may be off board the transport, may be accessible directly and/or through a network.

Figure 6A:
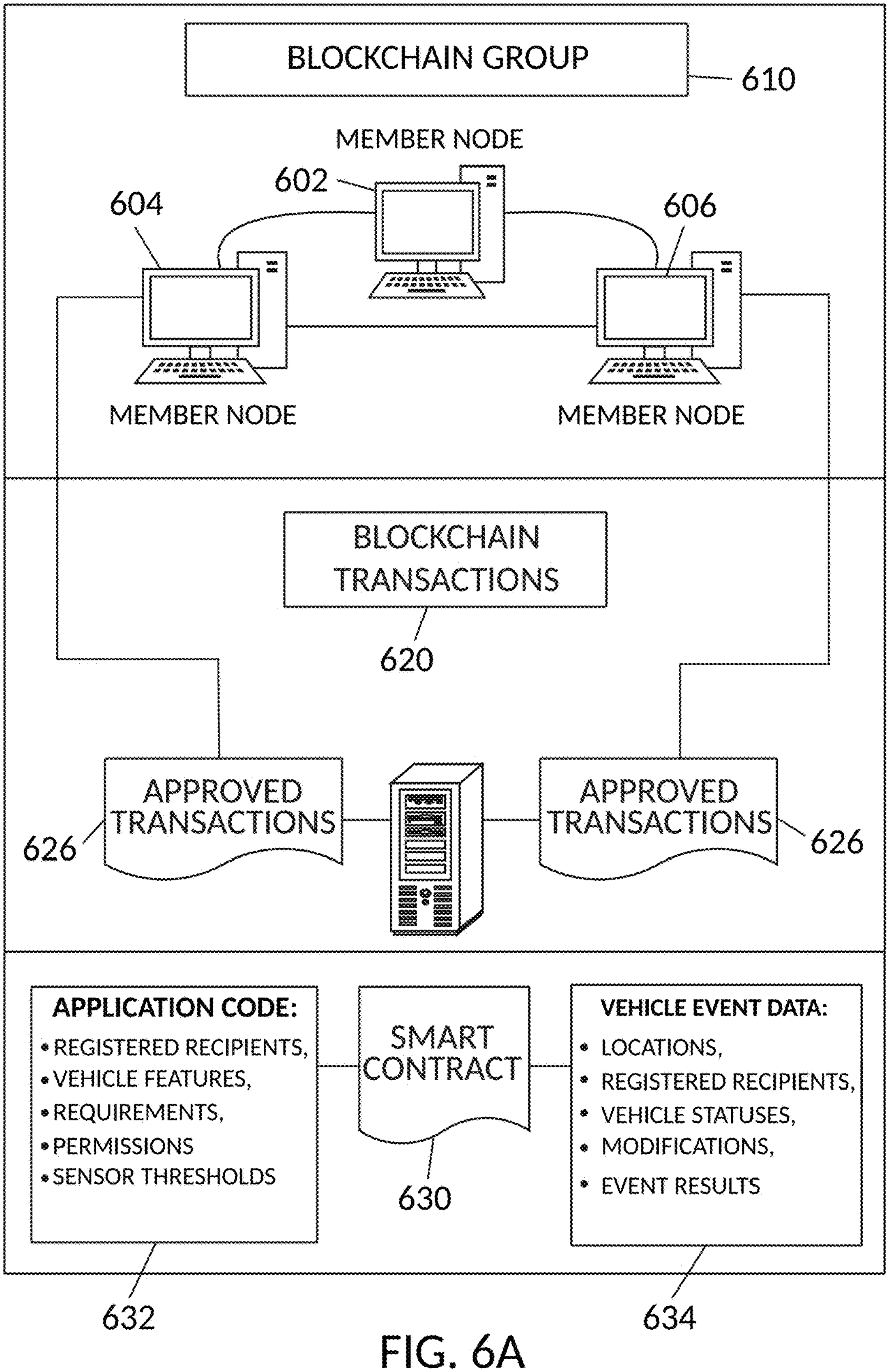
FIG. 6A illustrates a blockchain architecture configuration, according to example embodiments.

FIG. 6A illustrates a blockchain architecture configuration 600, according to example embodiments. Referring to FIG. 6A, the blockchain architecture 600 may include certain blockchain elements, for example, a group of blockchain member nodes 602-606 as part of a blockchain group 610. In one example embodiment, a permissioned blockchain is not accessible to all parties but only to those members with permissioned access to the blockchain data. The blockchain nodes participate in a number of activities, such as blockchain entry addition and validation process (consensus). One or more of the blockchain nodes may endorse entries based on an endorsement policy and may provide an ordering service for all blockchain nodes. A blockchain node may initiate a blockchain action (such as an authentication) and seek to write to a blockchain immutable ledger stored in the blockchain, a copy of which may also be stored on the underpinning physical infrastructure.

The blockchain transactions 620 are stored in memory of computers as the transactions are received and approved by the consensus model dictated by the members' nodes. Approved transactions 626 are stored in current blocks of the blockchain and committed to the blockchain via a committal procedure, which includes performing a hash of the data contents of the transactions in a current block and referencing a previous hash of a previous block. Within the blockchain, one or more smart contracts 630 may exist that define the terms of transaction agreements and actions included in smart contract executable application code 632, such as registered recipients, vehicle features, requirements, permissions, sensor thresholds, etc. The code may be configured to identify whether requesting entities are registered to receive vehicle services, what service features they are entitled/required to receive given their profile statuses and whether to monitor their actions in subsequent events. For example, when a service event occurs and a user is riding in the vehicle, the sensor data monitoring may be triggered, and a certain parameter, such as a vehicle charge level, may be identified as being above/below a particular threshold for a particular period of time, then the result may be a change to a current status, which requires an alert to be sent to the managing party (i.e., vehicle owner, vehicle operator, server, etc.) so the service can be identified and stored for reference. The vehicle sensor data collected may be based on types of sensor data used to collect information about vehicle's status. The sensor data may also be the basis for the vehicle event data 634, such as a location(s) to be traveled, an average speed, a top speed, acceleration rates, whether there were any collisions, was the expected route taken, what is the next destination, whether safety measures are in place, whether the vehicle has enough charge/fuel, etc. All such information may be the basis of smart contract terms 630, which are then stored in a blockchain. For example, sensor thresholds stored in the smart contract can be used as the basis for whether a detected service is necessary and when and where the service should be performed.

Figure 6B:
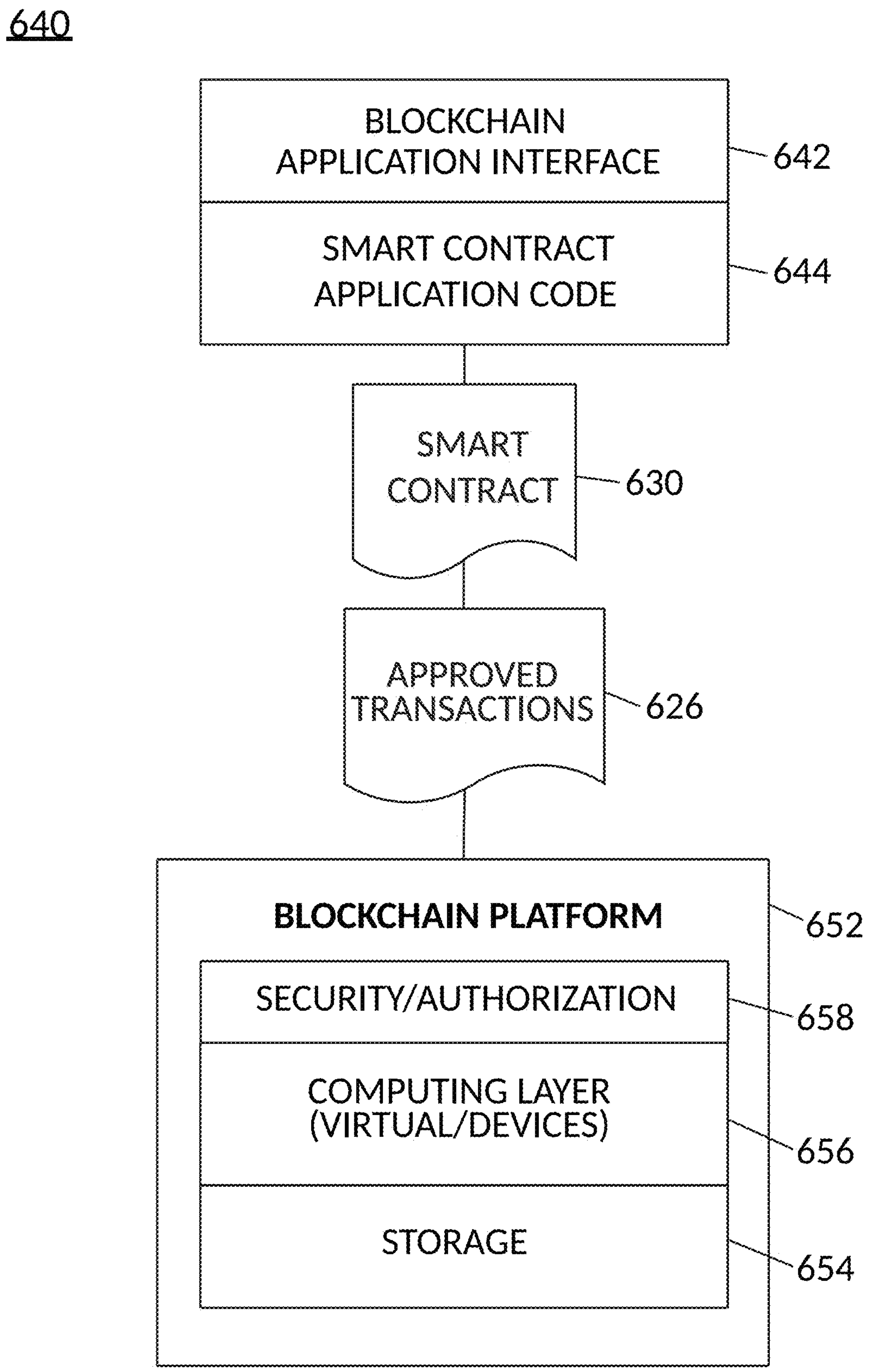
FIG. 6B illustrates another blockchain configuration, according to example embodiments.

FIG. 6B illustrates a shared ledger configuration, according to example embodiments. Referring to FIG. 6B, the blockchain logic example 640 includes a blockchain application interface 642 as an API or plug-in application that links to the computing device and execution platform for a particular transaction. The blockchain configuration 640 may include one or more applications, which are linked to application programming interfaces (APIs) to access and execute stored program/application code (e.g., smart contract executable code, smart contracts, etc.), which can be created according to a customized configuration sought by participants and can maintain their own state, control their own assets, and receive external information. This can be deployed as an entry and installed, via appending to the distributed ledger, on all blockchain nodes.

The smart contract application code 644 provides a basis for the blockchain transactions by establishing application code, which when executed causes the transaction terms and conditions to become active. The smart contract 630, when executed, causes certain approved transactions 626 to be generated, which are then forwarded to the blockchain platform 652. The platform includes a security/authorization 658, computing devices, which execute the transaction management 656 and a storage portion 654 as a memory that stores transactions and smart contracts in the blockchain.

The blockchain platform may include various layers of blockchain data, services (e.g., cryptographic trust services, virtual execution environment, etc.), and underpinning physical computer infrastructure that may be used to receive and store new entries and provide access to auditors, which are seeking to access data entries. The blockchain may expose an interface that provides access to the virtual execution environment necessary to process the program code and engage the physical infrastructure. Cryptographic trust services may be used to verify entries such as asset exchange entries and keep information private.

The blockchain architecture configuration of FIGS. 6A and 6B may process and execute program/application code via one or more interfaces exposed, and services provided, by the blockchain platform. As a non-limiting example, smart contracts may be created to execute reminders, updates, and/or other notifications subject to the changes, updates, etc. The smart contracts can themselves be used to identify rules associated with authorization and access requirements and usage of the ledger. For example, the information may include a new entry, which may be processed by one or more processing entities (e.g., processors, virtual machines, etc.) included in the blockchain layer. The result may include a decision to reject or approve the new entry based on the criteria defined in the smart contract and/or a consensus of the peers. The physical infrastructure may be utilized to retrieve any of the data or information described herein.

Within smart contract executable code, a smart contract may be created via a high-level application and programming language, and then written to a block in the blockchain. The smart contract may include executable code that is registered, stored, and/or replicated with a blockchain (e.g., distributed network of blockchain peers). An entry is an execution of the smart contract code, which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A smart contract executable code may include the code interpretation of a smart contract, with additional features. As described herein, the smart contract executable code may be program code deployed on a computing network, where it is executed and validated by chain validators together during a consensus process. The smart contract executable code receives a hash and retrieves from the blockchain a hash associated with the data template created by use of a previously stored feature extractor. If the hashes of the hash identifier and the hash created from the stored identifier template data match, then the smart contract executable code sends an authorization key to the requested service. The smart contract executable code may write to the blockchain data associated with the cryptographic details.

Figure 6C:
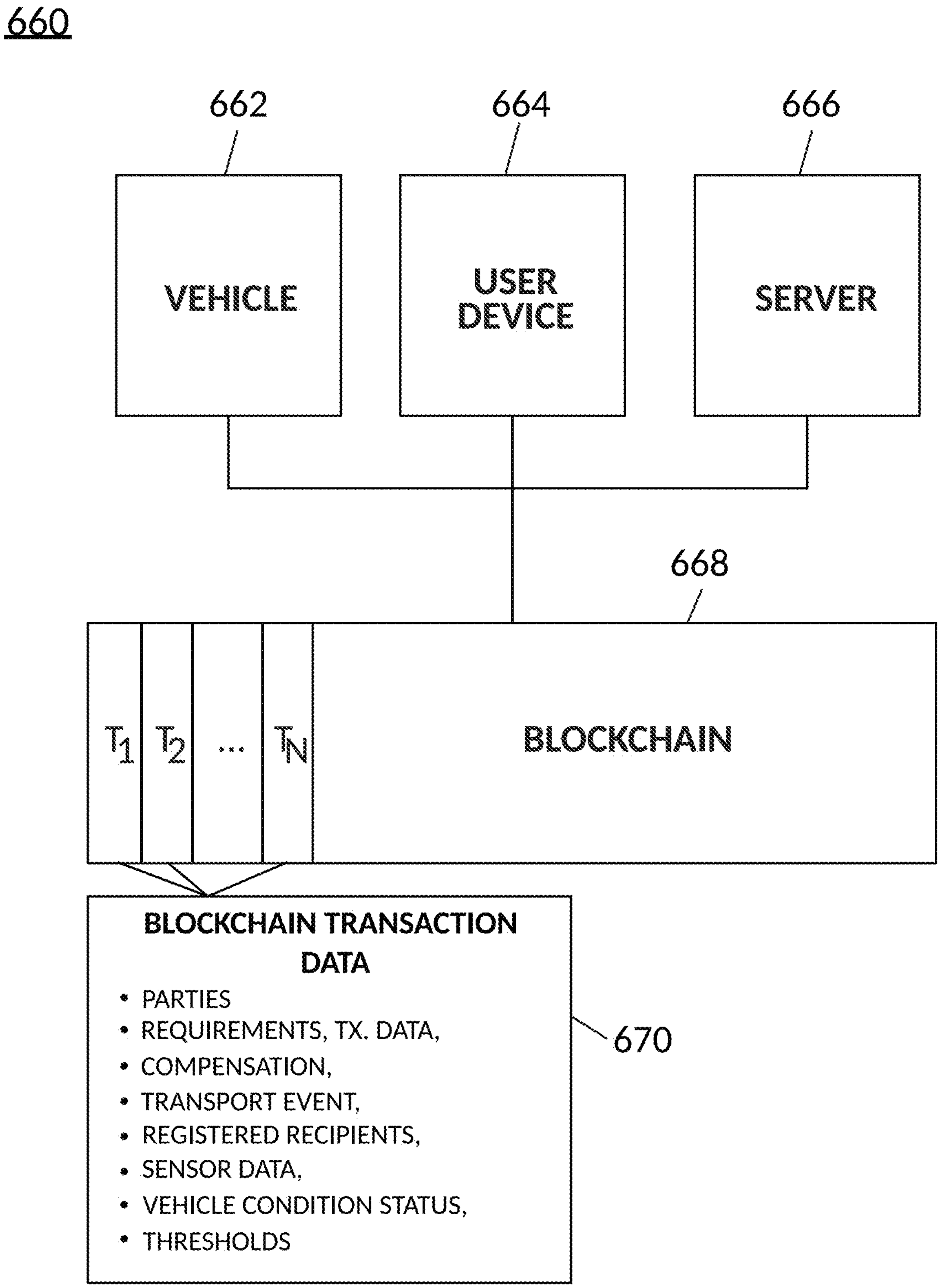
FIG. 6C illustrates a blockchain configuration for storing blockchain transaction data, according to example embodiments.

FIG. 6C illustrates a blockchain configuration for storing blockchain transaction data, according to example embodiments. Referring to FIG. 6C, the example configuration 660 provides for the vehicle 662, the user device 664 and a server 666 sharing information with a distributed ledger (i.e., blockchain) 668. The server may represent a service provider entity inquiring with a vehicle service provider to share user profile rating information in the event that a known and established user profile is attempting to rent a vehicle with an established rated profile. The server 666 may be receiving and processing data related to a vehicle's service requirements. As the service events occur, such as the vehicle sensor data indicates a need for fuel/charge, a maintenance service, etc., a smart contract may be used to invoke rules, thresholds, sensor information gathering, etc., which may be used to invoke the vehicle service event. The blockchain transaction data 670 is saved for each transaction, such as the access event, the subsequent updates to a vehicle's service status, event updates, etc. The transactions may include the parties, the requirements (e.g., 18 years of age, service eligible candidate, valid driver's license, etc.), compensation levels, the distance traveled during the event, the registered recipients permitted to access the event and host a vehicle service, rights/permissions, sensor data retrieved during the vehicle event operation to log details of the next service event and identify a vehicle's condition status, and thresholds used to make determinations about whether the service event was completed and whether the vehicle's condition status has changed.

Figure 6D:
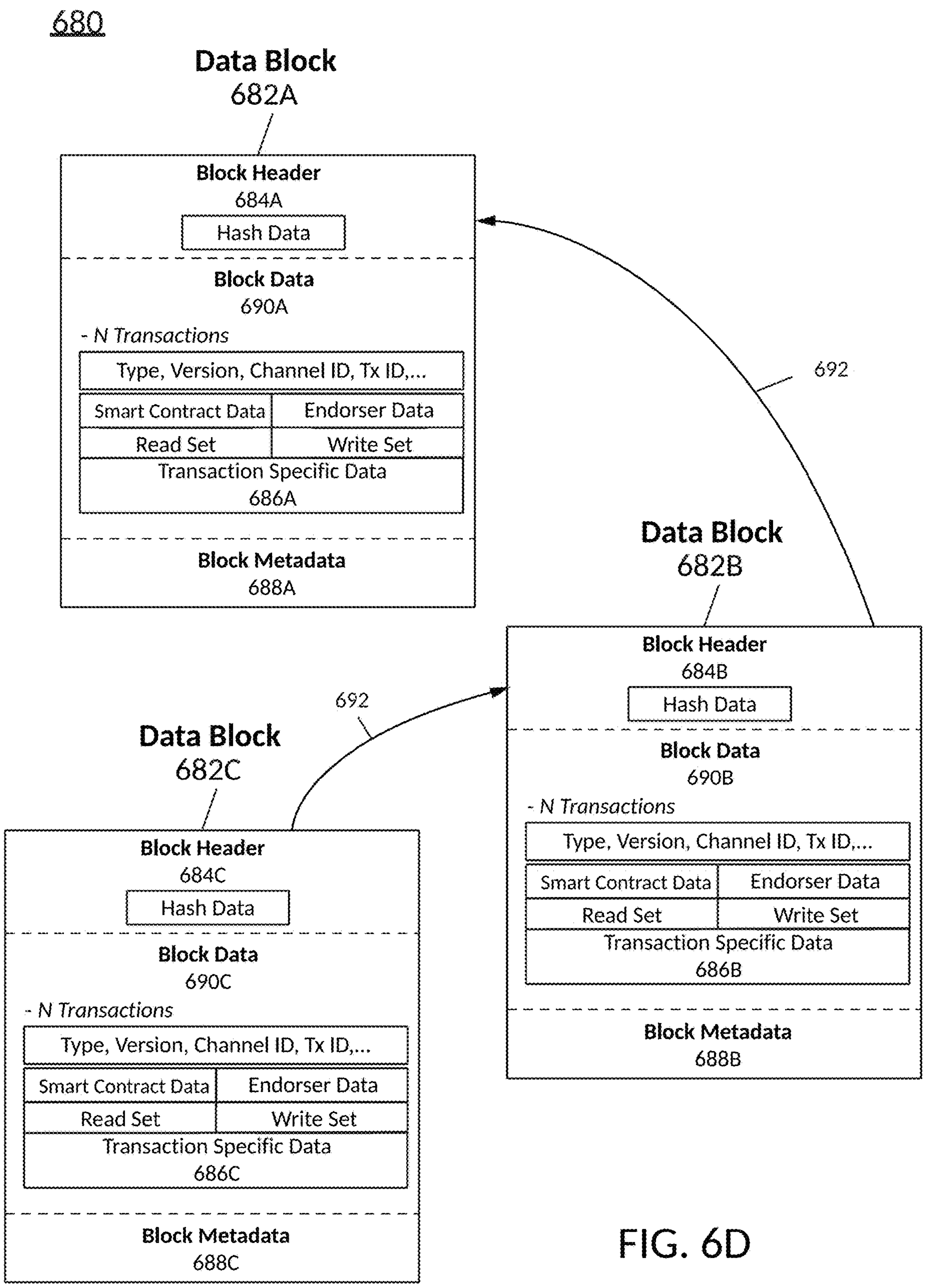
FIG. 6D illustrates example data blocks, according to example embodiments.

FIG. 6D illustrates blockchain blocks 680 that can be added to a distributed ledger, according to example embodiments, and contents of block structures 682A to 682*n*. Referring to FIG. 6D, clients (not shown) may submit entries to blockchain nodes to enact activity on the blockchain. As an example, clients may be applications that act on behalf of a requester, such as a device, person or entity to propose entries for the blockchain. The plurality of blockchain peers (e.g., blockchain nodes) may maintain a state of the blockchain network and a copy of the distributed ledger. Different types of blockchain nodes/peers may be present in the blockchain network including endorsing peers, which simulate and endorse entries proposed by clients and committing peers which verify endorsements, validate entries, and commit entries to the distributed ledger. In this example, the blockchain nodes may perform the role of endorser node, committer node, or both.

The instant system includes a blockchain that stores immutable, sequenced records in blocks, and a state database (current world state) maintaining a current state of the blockchain. One distributed ledger may exist per channel and each peer maintains its own copy of the distributed ledger for each channel of which they are a member. The instant blockchain is an entry log, structured as hash-linked blocks where each block contains a sequence of N entries. Blocks may include various components such as those shown in FIG. 6D. The linking of the blocks may be generated by adding a hash of a prior block's header within a block header of a current block. In this way, all entries on the blockchain are sequenced and cryptographically linked together preventing tampering with blockchain data without breaking the hash links. Furthermore, because of the links, the latest block in the blockchain represents every entry that has come before it. The instant blockchain may be stored on a peer file system (local or attached storage), which supports an append-only blockchain workload.

The current state of the blockchain and the distributed ledger may be stored in the state database. Here, the current state data represents the latest values for all keys ever included in the chain entry log of the blockchain. Smart contract executable code invocations execute entries against the current state in the state database. To make these smart contract executable code interactions extremely efficient, the latest values of all keys are stored in the state database. The state database may include an indexed view into the entry log of the blockchain, it can therefore be regenerated from the chain at any time. The state database may automatically get recovered (or generated if needed) upon peer startup, before entries are accepted.

Endorsing nodes receive entries from clients and endorse the entry based on simulated results. Endorsing nodes hold smart contracts, which simulate the entry proposals. When an endorsing node endorses an entry, the endorsing nodes creates an entry endorsement, which is a signed response from the endorsing node to the client application indicating the endorsement of the simulated entry. The method of endorsing an entry depends on an endorsement policy that may be specified within smart contract executable code. An example of an endorsement policy is "the majority of endorsing peers must endorse the entry." Different channels may have different endorsement policies. Endorsed entries are forward by the client application to an ordering service.

The ordering service accepts endorsed entries, orders them into a block, and delivers the blocks to the committing peers. For example, the ordering service may initiate a new block when a threshold of entries has been reached, a timer times out, or another condition. In this example, blockchain node is a committing peer that has received a data block 682A for storage on the blockchain. The ordering service may be made up of a cluster of orderers. The ordering service does not process entries, smart contracts, or maintain the shared ledger. Rather, the ordering service may accept the endorsed entries and specifies the order in which those entries are committed to the distributed ledger. The architecture of the blockchain network may be designed such that the specific implementation of 'ordering' (e.g., Solo, Kafka, BFT, etc.) becomes a pluggable component.

Entries are written to the distributed ledger in a consistent order. The order of entries is established to ensure that the updates to the state database are valid when they are committed to the network. Unlike a cryptocurrency blockchain system (e.g., Bitcoin, etc.) where ordering occurs through the solving of a cryptographic puzzle, or mining, in this example the parties of the distributed ledger may choose the ordering mechanism that best suits that network.

Referring to FIG. 6D, a block 682A (also referred to as a data block) that is stored on the blockchain and/or the distributed ledger may include multiple data segments such as a block header 684A to 684*n*, transaction specific data 686A to 686*n*, and block metadata 688A to 688*n*. It should be appreciated that the various depicted blocks and their contents, such as block 682A and its contents are merely for purposes of an example and are not meant to limit the scope of the example embodiments. In some cases, both the block header 684A and the block metadata 688A may be smaller than the transaction specific data 686A, which stores entry data; however, this is not a requirement. The block 682A may store transactional information of N entries (e.g., 100, 500, 1000, 2000, 3000, etc.) within the block data 690A to 690*n*. The block 682A may also include a link to a previous block (e.g., on the blockchain) within the block header 684A. In particular, the block header 684A may include a hash of a previous block's header. The block header 684A may also include a unique block number, a hash of the block data 690A of the current block 682A, and the like. The block number of the block 682A may be unique and assigned in an incremental/sequential order starting from zero. The first block in the blockchain may be referred to as a genesis block, which includes information about the blockchain, its members, the data stored therein, etc.

The block data 690A may store entry information of each entry that is recorded within the block. For example, the entry data may include one or more of a type of the entry, a version, a timestamp, a channel ID of the distributed ledger, an entry ID, an epoch, a payload visibility, a smart contract executable code path (deploy tx), a smart contract executable code name, a smart contract executable code version, input (smart contract executable code and functions), a client (creator) identify such as a public key and certificate, a signature of the client, identities of endorsers, endorser signatures, a proposal hash, smart contract executable code events, response status, namespace, a read set (list of key and version read by the entry, etc.), a write set (list of key and value, etc.), a start key, an end key, a list of keys, a Merkel tree query summary, and the like. The entry data may be stored for each of the N entries.

In some embodiments, the block data 690A may also store transaction specific data 686A, which adds additional information to the hash-linked chain of blocks in the blockchain. Accordingly, the data 686A can be stored in an immutable log of blocks on the distributed ledger. Some of the benefits of storing such data 686A are reflected in the various embodiments disclosed and depicted herein. The block metadata 688A may store multiple fields of metadata (e.g., as a byte array, etc.). Metadata fields may include signature on block creation, a reference to a last configuration block, an entry filter identifying valid and invalid entries within the block, last offset persisted of an ordering service that ordered the block, and the like. The signature, the last configuration block, and the orderer metadata may be added by the ordering service. Meanwhile, a committer of the block (such as a blockchain node) may add validity/invalidity information based on an endorsement policy, verification of read/write sets, and the like. The entry filter may include a byte array of a size equal to the number of entries in the block data 610A and a validation code identifying whether an entry was valid/invalid.

The other blocks 682B to 682*n* in the blockchain also have headers, files, and values. However, unlike the first block 682A, each of the headers 684A to 684*n* in the other blocks includes the hash value of an immediately preceding block. The hash value of the immediately preceding block may be just the hash of the header of the previous block or may be the hash value of the entire previous block. By including the hash value of a preceding block in each of the remaining blocks, a trace can be performed from the Nth block back to the genesis block (and the associated original file) on a block-by-block basis, as indicated by arrows 692, to establish an auditable and immutable chain-of-custody.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 7 illustrates an example computer system architecture 700, which may represent or be integrated in any of the above-described components, etc.

Figure 7:
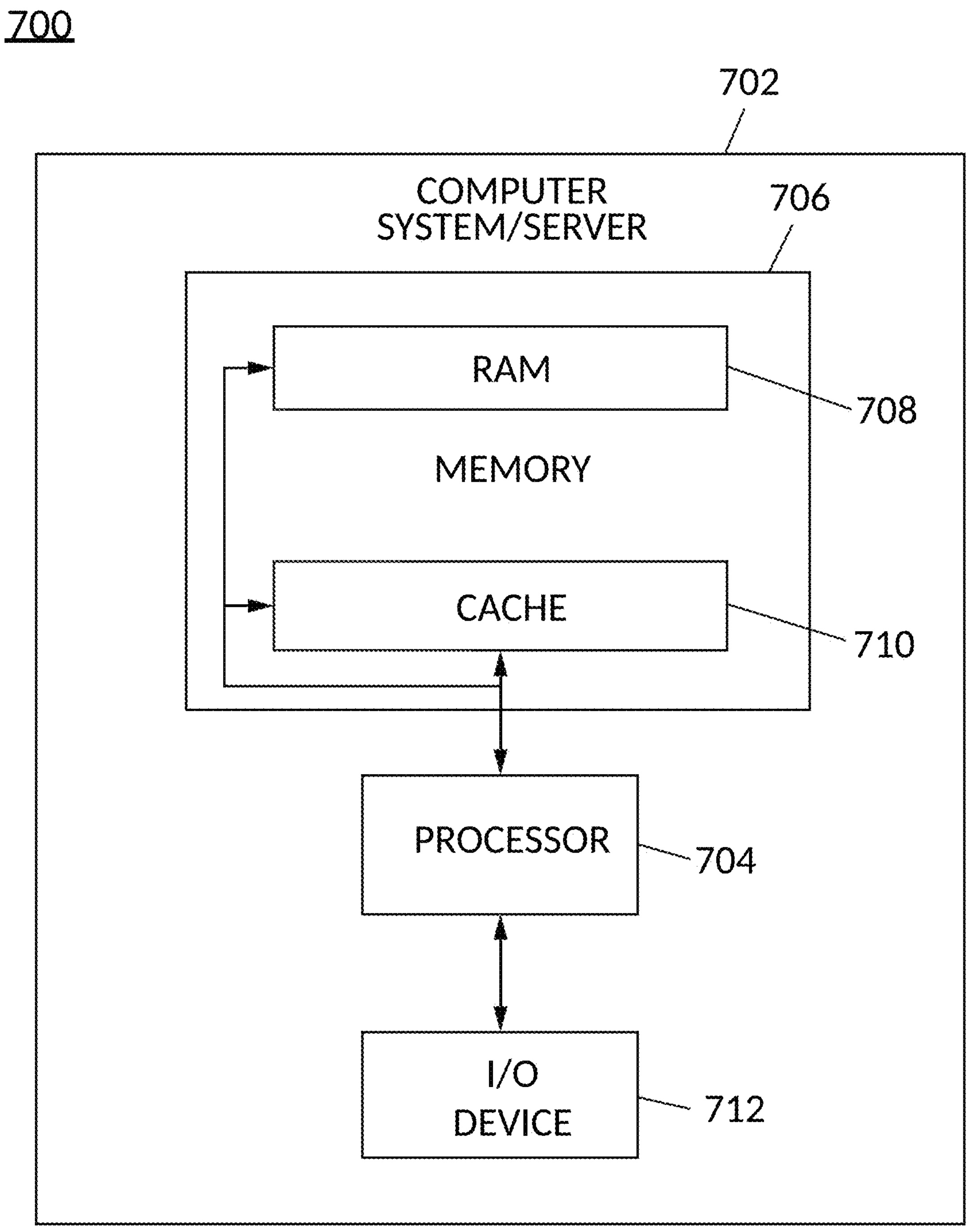
FIG. 7 illustrates an example system that supports one or more of the example embodiments.

FIG. 7 is not intended to suggest any limitation as to the scope of use or functionality of embodiments of the application described herein. Regardless, the computing node 700 is capable of being implemented and/or performing any of the functionality set forth hereinabove.

In computing node 700 there is a computer system/server 702, which is operational with numerous other general purpose or special purpose computing system environments or configurations. Examples of well-known computing systems, environments, and/or configurations that may be suitable for use with computer system/server 702 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 702 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 702 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 702 in cloud computing node 700 is shown in the form of a general-purpose computing device. The components of computer system/server 702 may include, but are not limited to, one or more processors or processing units 704, a system memory 706, and a bus that couples various system components including system memory 706 to processor 704.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 702 typically includes a variety of computer system readable media. Such media may be any available media that is accessible by computer system/server 702, and it includes both volatile and non-volatile media, removable and non-removable media. System memory 706, in one embodiment, implements the flow diagrams of the other figures. The system memory 706 can include computer system readable media in the form of volatile memory, such as random-access memory (RAM) 708 and/or cache memory 710. Computer system/server 702 may further include other removable/non-removable, volatile/non-volatile computer system storage media. By way of example only, memory 706 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 706 may include at least one program product having a set (e.g., at least one) of program modules that are configured to carry out the functions of various embodiments of the application.

Program/utility, having a set (at least one) of program modules, may be stored in memory 706 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 702 may also communicate with one or more external devices via an I/O device 712 (such as an I/O adapter), which may include a keyboard, a pointing device, a display, a voice recognition module, etc., one or more devices that enable a user to interact with computer system/server 702, and/or any devices (e.g., network card, modem, etc.) that enable computer system/server 702 to communicate with one or more other computing devices. Such communication can occur via I/O interfaces of the device 712. Still yet, computer system/server 702 can communicate with one or more networks such as a local area network (LAN), a general wide area network (WAN), and/or a public network (e.g., the Internet) via a network adapter. As depicted, device 712 communicates with the other components of computer system/server 702 via a bus. It should be understood that although not shown, other hardware and/or software components could be used in conjunction with computer system/server 702. Examples, include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations that when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method, comprising:

identifying, by a processor, that a level of a reaction of an occupant of a transport in response to displaying data on a display is greater than a threshold value;

modifying, by the processor, an operational setting of a subsystem within a cabin of the transport to reduce the level of the reaction; and identifying, by the processor, whether modification to the operational setting has reduced the level of the reaction.

2. The method of claim 1, comprising:

in response to the level of the reaction being greater than the threshold value, sending a message to another transport proximate to the transport.

3. The method of claim 1, comprising:

in response to the level of the reaction being greater than the threshold value:

altering a path of the transport by the processor; and
sending a message to another transport proximate to the transport to control the another transport to alter its path.

4. The method of claim 1, comprising:
detecting by the processor that the occupant has exited and reoccupied the transport; and
in response to the detecting that the occupant has reoccupied the transport, repeating the modification of the operational setting of the transport to reduce the level of the reaction below a previous level of the reaction.

5. The method of claim 1, comprising:
routing the transport to a medical facility when the level of the reaction continues to increase past the threshold value.

6. The method of claim 1, comprising:
sending, by the processor, a notification of the level of the reaction and the data to the display;
wherein the notification comprises a recommended course of action to reduce the level of the reaction.

7. The method of claim 1, comprising:
modifying the threshold value by the processor based on a condition affecting the level of the reaction of the occupant.

8. A transport, comprising:
a processor that, when executing instructions stored in an associated memory, is configured to:
identify that a level of a reaction of an occupant of a transport in response to data being displayed on a display is greater than a threshold value;
modify an operational setting of a subsystem within a cabin of the transport to reduce the level of the reaction; and
identify whether modification to the operational setting has reduced the level of the reaction.

9. The transport of claim 8, wherein the processor is further configured to:
in response to the level of the reaction being greater than the threshold value, send a message to another transport proximate to the transport.

10. The transport of claim 8, wherein the processor is further configured to:
in response to the level of the reaction being greater than the threshold value:
alter a path of the transport; and
send a message to another transport proximate to the transport to control the another transport to alter its path.

11. The transport of claim 8, wherein the processor is further configured to:
detect that the occupant has exited and reoccupied the transport; and
in response to the detection that the occupant has reoccupied the transport, repeat the modification of the operational setting of the transport to reduce the level of the reaction below a previous level of the reaction.

12. The transport of claim 8, wherein the processor is further configured to:
route the transport to a medical facility when the level of the reaction continues to increase past the threshold value.

13. The transport of claim 8, wherein the processor is further configured to:
send a notification of the level of the reaction and the data to the display;
wherein the notification comprises a recommended course of action to reduce the level of the reaction.

14. The transport of claim 8, wherein the processor is further configured to:
modify the threshold value by the processor based on a condition that affects the level of the reaction of the occupant.

15. A non-transitory computer-readable medium comprising instructions that, when executed by a processor of a transport, cause the processor to perform:
identifying that a level of a reaction of an occupant of a transport in response to displaying data on a display is greater than a threshold value;
modifying an operational setting of a subsystem within a cabin of the transport to reduce the level of the reaction; and
identifying whether modification to the operational setting has reduced the level of the reaction.

16. The non-transitory computer-readable medium of claim 15, wherein the instructions further cause the processor to perform:
in response to the level of the reaction being greater than the threshold value, sending a message to another transport proximate to the transport altering, by the transport, a path of the transport to alter the level of the reaction towards the threshold value; and notifying other transports proximate the transport of the altered path.

17. The non-transitory computer-readable medium of claim 15, wherein the instructions further cause the processor to perform:
in response to the level of the reaction being greater than the threshold value:
altering a path of the transport; and
sending a message to another transport proximate to the transport to control the another transport to alter its path.

18. The non-transitory computer-readable medium of claim 15, wherein the instructions further cause the processor to perform:
detecting that the occupant has exited and reoccupied the transport; and
in response to the detecting that the occupant has reoccupied the transport, repeating the modification of the operational setting of the transport to reduce the level of the reaction below a previous level of the reaction.

19. The non-transitory computer-readable medium of claim 15, wherein the instructions further cause the processor to perform:
routing the transport to a medical facility when the level of the reaction continues to increase past the threshold value.

20. The non-transitory computer-readable medium of claim 15, wherein the instructions further cause the processor to perform:
modifying the threshold value based on a condition affecting the level of the reaction of the occupant.

* * * * *